(12) United States Patent
Wang et al.

(10) Patent No.: US 8,215,157 B2
(45) Date of Patent: Jul. 10, 2012

(54) SYSTEM AND METHOD FOR MEASURING LIQUID VISCOSITY IN A FLUID DELIVERY SYSTEM

(75) Inventors: Jong H. Wang, Rancho Palos Verdes, CA (US); Siddharth B. Desai, Ladera Ranch, CA (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 855 days.

(21) Appl. No.: 12/244,411

(22) Filed: Oct. 2, 2008

(65) Prior Publication Data
US 2009/0113996 A1    May 7, 2009

Related U.S. Application Data

(60) Provisional application No. 60/977,517, filed on Oct. 4, 2007.

(51) Int. Cl.
*G01N 11/00* (2006.01)
(52) U.S. Cl. .................................. 73/54.43
(58) Field of Classification Search ............... 73/54.43, 73/54.01, 54.02
See application file for complete search history.

(56) References Cited

U.S. PATENT DOCUMENTS

| | | | |
|---|---|---|---|
| 4,363,321 A | 12/1982 | Chittenden | 604/31 |
| 4,619,653 A | 10/1986 | Fischell | 604/891.1 |
| 4,645,489 A | 2/1987 | Krumme et al. | 604/245 |
| 4,654,813 A | 3/1987 | Edlund et al. | 702/198 |
| 5,061,243 A | 10/1991 | Winchell et al. | 604/132 |
| 5,069,668 A | 12/1991 | Boydman | 604/121 |
| 5,395,320 A | 3/1995 | Padda et al. | 604/65 |
| 5,672,832 A | 9/1997 | Cucci et al. | 73/861.52 |
| 5,834,314 A | 11/1998 | Gates et al. | 436/52 |
| 5,861,561 A | 1/1999 | Van Cleve et al. | 73/861.52 |
| 5,897,530 A | 4/1999 | Jackson | 604/132 |
| 5,976,085 A | 11/1999 | Kimball et al. | 600/309 |

(Continued)

FOREIGN PATENT DOCUMENTS
DE    4308313    9/1994
(Continued)

OTHER PUBLICATIONS

International Search Report for PCT/US2005/016526 (corresponds to U.S. application published as US 2005/0267413) (Dec. 22, 2005, 6 pages).

(Continued)

*Primary Examiner* — Hezron E Williams
*Assistant Examiner* — Tamiko Bellamy
(74) *Attorney, Agent, or Firm* — Marshall, Gerstein & Borun LLP

(57) ABSTRACT

The present invention includes systems and methods for determining the viscosity of a fluid within a fluid flow path. Such method may comprise flowing fluid through the fluid flow path and past a fixed flow restriction therein. The method may also comprise first sensing of a fluid pressure within the fluid flow path at a selected location upstream of the flow restriction. The method may also include limiting fluid flow in the fluid flow path upstream of such selected location. The method may further comprise second sensing of a fluid pressure within the fluid flow path at such selected location after such limiting. Such method includes determining the viscosity of the fluid based, at least in part, on any pressure difference from such first and second sensing.

6 Claims, 14 Drawing Sheets

U.S. PATENT DOCUMENTS

| | | | |
|---|---|---|---|
| 6,010,483 A | 1/2000 | Spencer | 604/151 |
| 6,231,560 B1 | 5/2001 | Bui et al. | 604/500 |
| 6,280,408 B1 | 8/2001 | Sipin | 604/65 |
| 6,290,681 B1 | 9/2001 | Brown | 604/246 |
| 6,685,668 B1 | 2/2004 | Cho et al. | 604/65 |
| 6,807,965 B1 | 10/2004 | Hickle | 128/204.23 |
| 6,813,964 B1 | 11/2004 | Clark et al. | 73/861.52 |
| 2002/0156464 A1 | 10/2002 | Blischak et al. | 604/892.1 |
| 2003/0040722 A1 | 2/2003 | Massengale et al. | 604/255 |
| 2003/0100863 A1 | 5/2003 | Shekalim | 604/141 |
| 2003/0216683 A1 | 11/2003 | Shekalim | 604/67 |
| 2004/0177703 A1 | 9/2004 | Schumacher et al. | 73/861.52 |
| 2005/0011282 A1 | 1/2005 | Voege et al. | 73/861.44 |
| 2005/0099363 A1 | 5/2005 | Yamamoto et al. | 345/33 |
| 2005/0177096 A1 | 8/2005 | Bollish et al. | 604/65 |
| 2005/0187515 A1 | 8/2005 | Varrichio et al. | 604/67 |
| 2005/0191196 A1 | 9/2005 | Tanner et al. | 417/477.2 |
| 2005/0267413 A1 | 12/2005 | Wang et al. | 604/131 |
| 2007/0112328 A1 | 5/2007 | Steinbach et al. | 604/500 |
| 2009/0093774 A1 | 4/2009 | Wang et al. | 604/247 |
| 2009/0221986 A1 | 9/2009 | Wang et al. | 604/503 |

FOREIGN PATENT DOCUMENTS

| | | |
|---|---|---|
| JP | 2004317367 A * | 11/2004 |
| WO | WO 00/47255 | 8/2000 |
| WO | WO 2005/056087 | 6/2005 |
| WO | WO 2007/033025 | 3/2007 |
| WO | WO 2009/046182 | 4/2009 |

OTHER PUBLICATIONS

Written Opinion for PCT/US2005/016526 (corresponds to U.S. application published as US 2005/0267413) (Dec. 22, 2005, 10 pages).

International Preliminary Report on Patentability for PCT/US2005/016526 (corresponds to U.S. application published as US 2005/0267413) (Nov. 29, 2006, 11 pages).

* cited by examiner

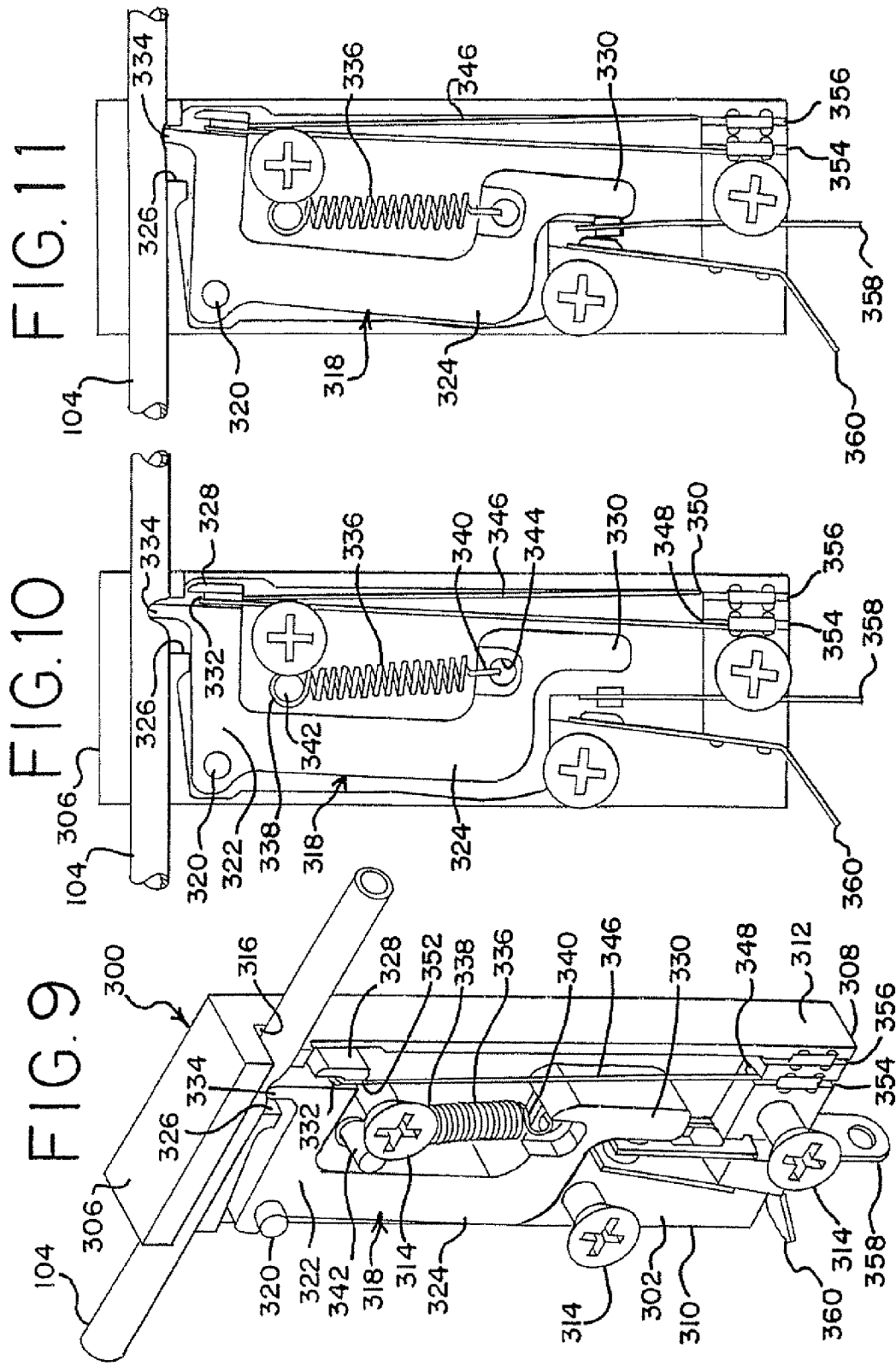

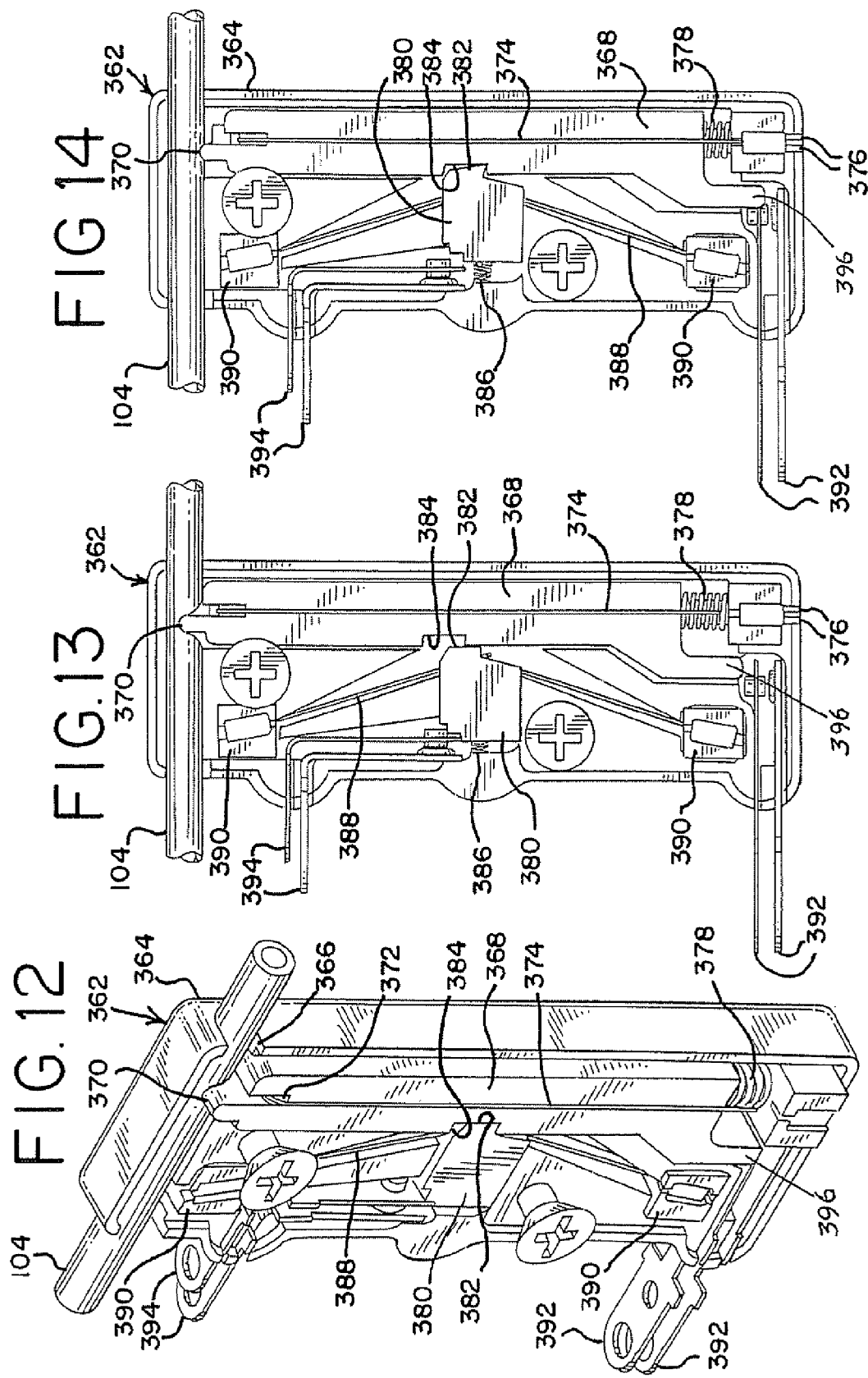

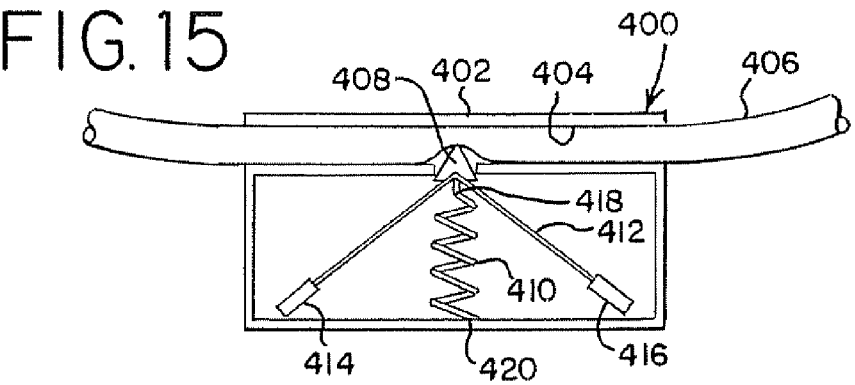
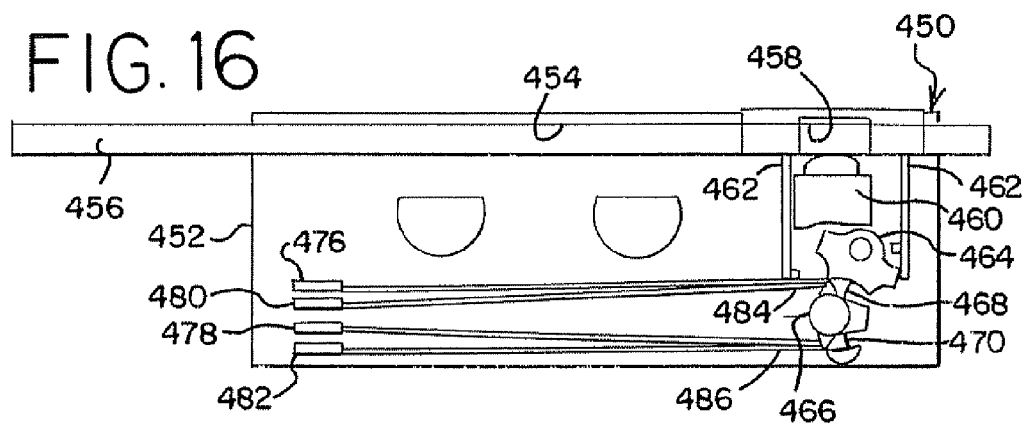
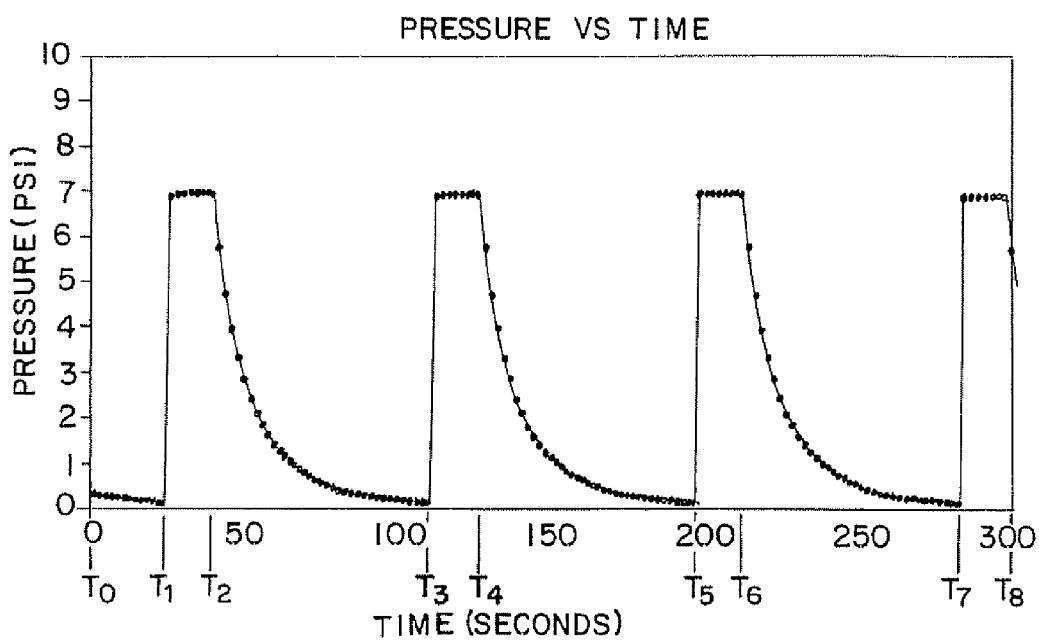

EFFECTS OF PULSE MODULATION ON FLOW RATE

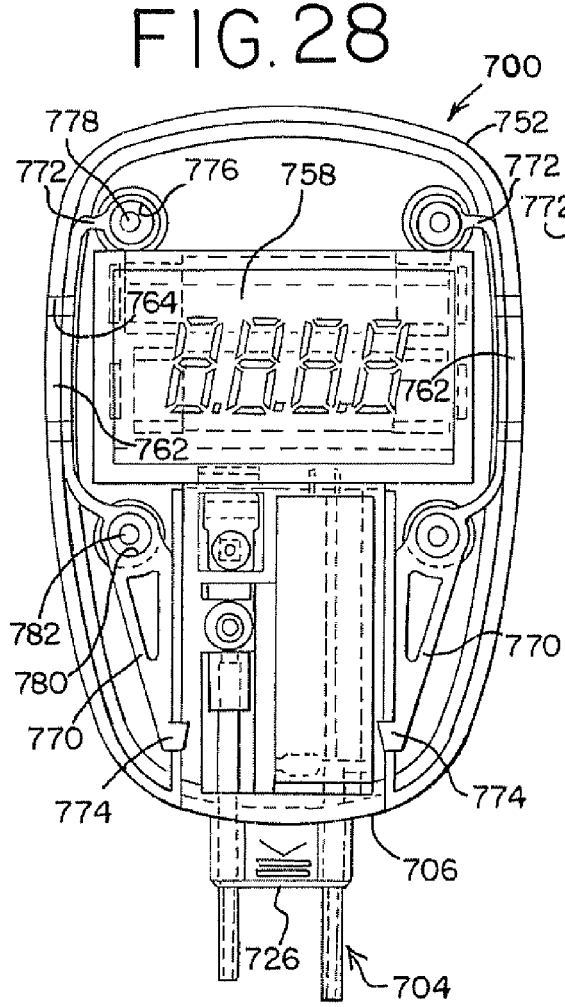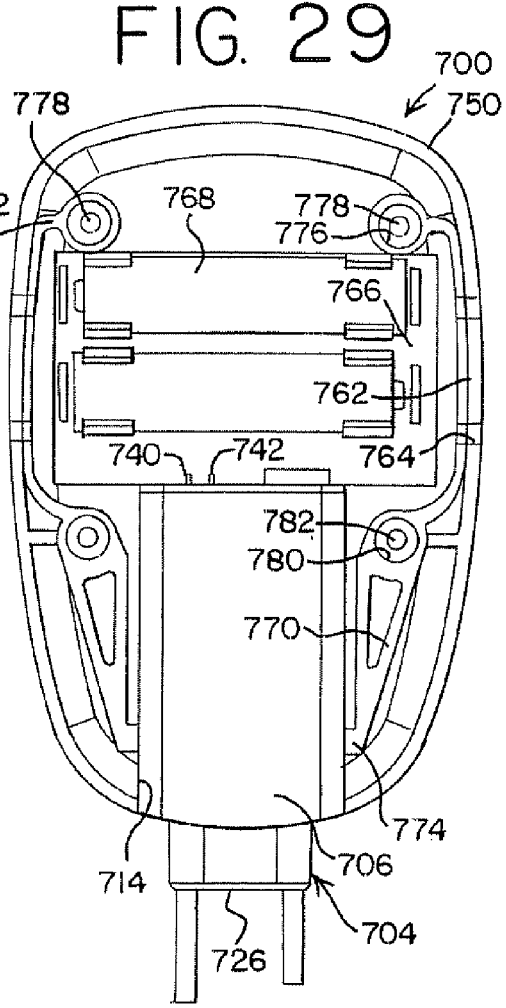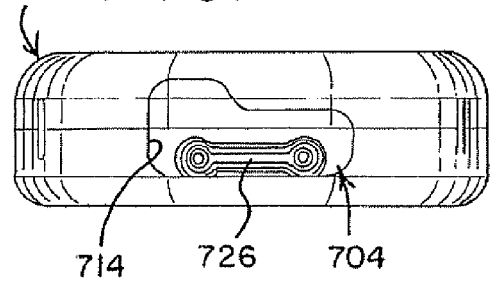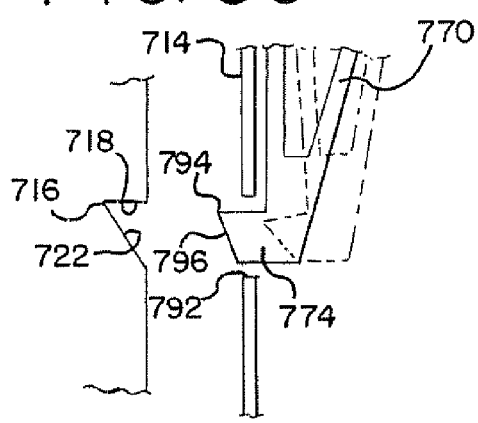

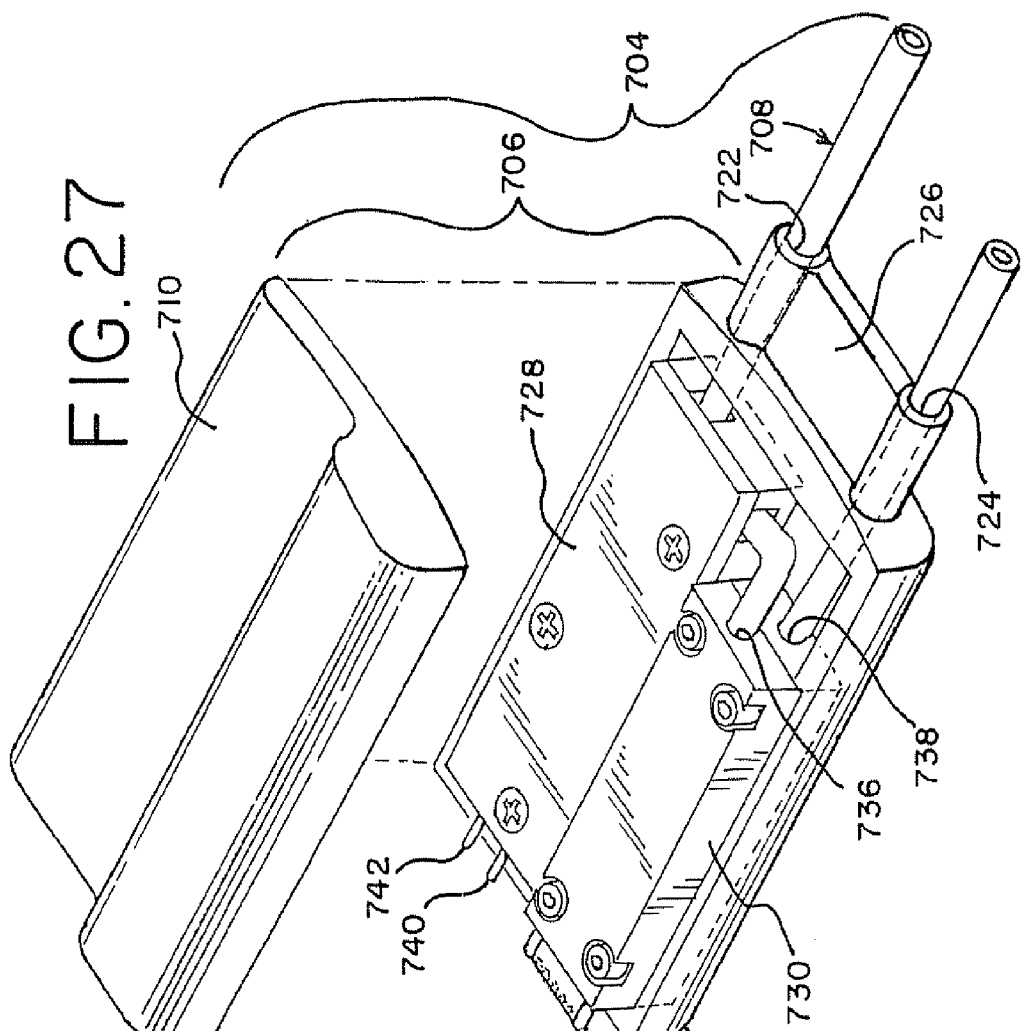
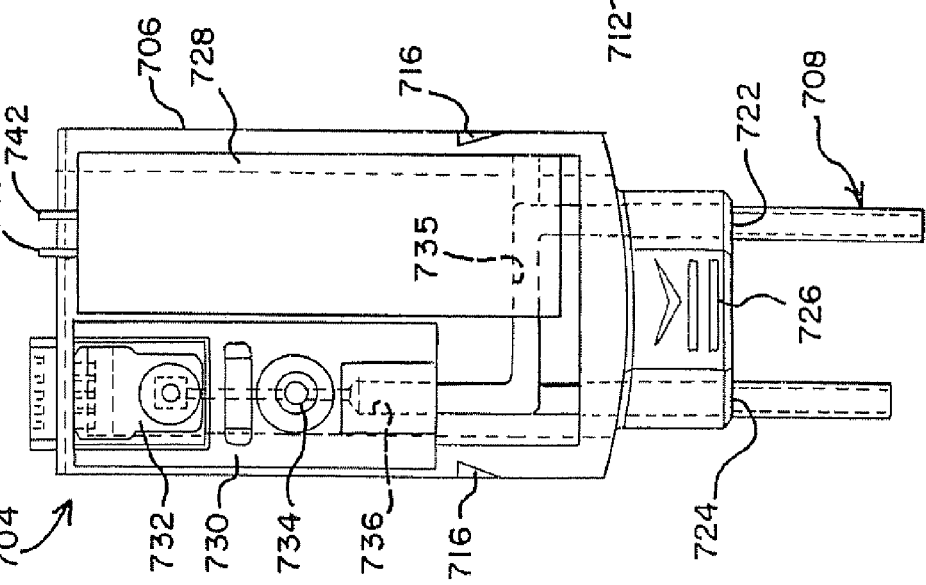

SYSTEM AND METHOD FOR MEASURING LIQUID VISCOSITY IN A FLUID DELIVERY SYSTEM

This invention generally relates to a medical fluid delivery system and its method of use.

It is common to intravenously administer or infuse medical liquids of various types to patients for therapeutic treatment, pain management and/or other reasons. The liquid or fluid may include a pharmaceutically active agent or drug, saline, nutritional fluid or other liquids. Such an infusion system may deliver fluid to the patient through a disposable flow circuit over a selected time period according to a programmed flow rate, or flow profile. While it is common for such infusion to be performed in a hospital environment where the patient is largely confined to a bed, if the infusion occurs over a long time period, it may be more convenient for the infusion be performed while the patient remains ambulatory.

In ambulatory as well as other medical fluid infusion systems, it is desirable for the flow rate to be accurate over the entire infusion period for administration of the prescribed amount of drug, medication or other medical fluid. However, certain prior art systems experience a change or reduction in the fluid flow rate as the amount of fluid in the source, e.g., a bag or other container, is exhausted.

Also, infusion systems are often used with fluids of differing viscosity, which further complicates the ability of the system to administer the desired flow rate of a given fluid. Calibration or design of a system to work with a certain average viscosity results in a variation when the fluid being administered has a different viscosity. To achieve a more accurate measure of the flow rate, certain prior art infusion systems require that the viscosity of the administered fluid be entered by the user into an infusion control system. However, this may be inconvenient or subject to error in the event viscosity is not known or available to user or, even if known, may not be accurate due to changes in temperature of the fluid in the system.

Also, prior art ambulatory infusion systems may not provide monitoring and adjustment of the actual flow rate during a particular fluid delivery therapy. For example, such systems generally may not allow the actual flow rate to be adjusted during a fluid delivery therapy as desired for a particular patient. Such control may be particularly useful in situations where the flow rate needs to be adjusted from time to time, such as in a system for administering pain control medication where the flow rate needs to change according to a level of pain being experienced by the patient.

Prior art ambulatory infusion systems further typically limit the ability of the patient to change or vary the flow rate of fluid delivery during a fluid delivery therapy. For example, a patient may need to slow or stop fluid delivery if the patient has an adverse reaction to the delivery fluid. Alternatively, the patient may require fluid delivery to be increased such as in a pain management therapy in response to pain that is sensed by the patient.

The factors described above make it evident that there are still unmet needs in the field of medical fluid administration for systems and methods that address one or more of the above-stated or other shortcomings.

SUMMARY OF THE INVENTION

In one aspect of the present invention, a medical fluid delivery system may be provided for determining viscosity of a fluid. Such system may comprise a fluid flow path for communicating between a source and a patient. Such system also may include a fixed flow restriction in the fluid flow path and a flow valve operatively associated with the fluid flow path upstream of the fixed flow restriction. Such valve may be movable between a first position, which allows fluid flow through the path, and a second position, which limits fluid flow through the fluid flow path. A control module may be operatively associated with the fluid flow path for sensing a fluid pressure difference within the fluid flow path at a selected location upstream of the flow restriction when the valve moves from the first position to the second position and for determining viscosity of the fluid based at least in part on such fluid pressure difference.

In another aspect of the present invention, a method may be provided for determining the viscosity of a fluid within a fluid flow path. Such method may comprise flowing fluid through the fluid flow path and past a fixed flow restriction therein. The method may also comprise first sensing of a fluid pressure within the fluid flow path at a selected location upstream of the flow restriction. The method may also include limiting fluid flow in the fluid flow path upstream of such selected location. The method may further comprise second sensing of a fluid pressure within the fluid flow path at such selected location after such limiting. Such method includes determining the viscosity of the fluid based, at least in part, on any pressure difference from such first and second sensing.

This summary is not intended as an exhaustive identification of each aspect or feature of the present invention that is now or may hereafter be claimed, but represents a summary of certain aspects of the present invention to assist in understanding the more detailed description that follows. Additional aspects or features of the present invention may be set forth in the following description.

Although described later in terms of certain structures, it should be understood that the apparatus, system and/or method of the present invention are not limited to the identical structures shown, and that the scope of the present invention is defined by the claims as now or hereafter filed.

BRIEF DESCRIPTION OF THE DRAWINGS

FIG. 9 is a perspective view of a flow non-latching valve with portions removed to show the interior components.

FIG. 10 is a front view of the flow valve shown in a closed position, which limits fluid flow through a fluid flow path.

FIG. 11 is a front view of the flow valve in FIG. 9, which is similar to FIG. 10, except showing such valve in an open position to allow fluid flow through the fluid flow path.

FIG. 12 is a perspective view of an alternate flow latching valve with portions removed to show the interior components.

FIG. 13 is a front view of the flow valve in FIG. 12 shown in a closed position, which limits fluid flow through a fluid flow path.

FIG. 14 is a front view of the flow valve in FIG. 12, which is similar to FIG. 13, except showing such valve in an open position to allow fluid flow through the fluid flow path.

FIG. 15 is a front view of another alternate flow regulator valve.

FIG. 16 is a front view of a further alternate flow regulator valve.

FIG. 19 is a graph showing pressure (in psi) versus time (in seconds) in accordance with the use of the present invention.

FIG. 25 is an end view of the system shown in FIG. 23.

FIG. 26 is an enlarged view of a disposable flow set showing portions of the disposable flow set removed to illustration some internal components, such as a flow valve, flow restriction and flow sensor and a portion of a fluid flow path.

FIG. 27 is an exploded perspective view of the disposable flow set shown in FIGS. 23-24 with the top housing portion shown removed.

FIG. 28 is a front view of the system shown in FIG. 23 with a front housing portion shown removed.

FIG. 29 is a bottom view of the system shown in FIG. 23 with a rear housing portion shown removed.

FIG. 30 is a partial enlarged view of the removable connection between the reusable controller and the disposable flow set with the distance between the controller and the flow set exaggerated to show the connection formed therebetween.

DESCRIPTION OF THE PREFERRED EMBODIMENTS

While the present invention will be described in terms of certain preferred or alternative embodiments, it is contemplated that the present invention may employ various structures, modifications and alternatives and that the scope of the invention is as set forth in the attached claims.

System Overview

Figure 1:
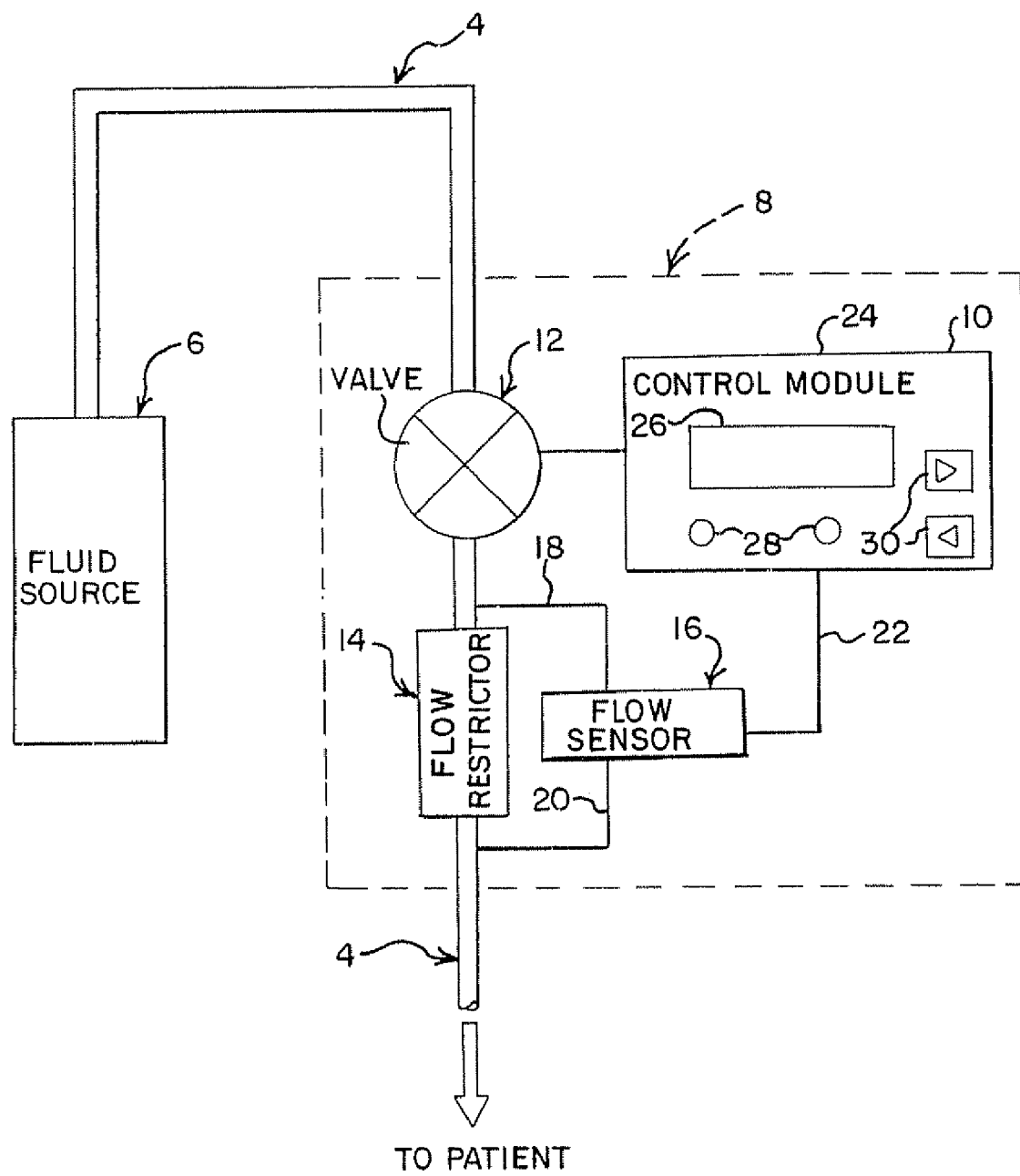
FIG. 1 is a schematic representation of one embodiment of an ambulatory fluid delivery system of the present invention showing a fluid source, a fluid flow path and a control system which includes a control module, a flow valve, a flow restrictor and a flow sensor.

In accordance with one embodiment of the present invention, FIG. 1 is a schematic representation of a fluid delivery system embodying the present invention, preferably an ambulatory fluid delivery system, generally indicated at 2, for delivering a medical fluid to a patient. It is noted that the fluid delivery system in FIG. 1 is shown schematically to illustrate certain broader aspects of the present invention, not limited to particular structures illustrated in more detailed figures. In FIG. 1, the system 2 includes a fluid flow path, generally indicated at 4, which communicates between a fluid source, generally indicated at 6, and the patient, via a needle, needleless cannula or other patient access device. The fluid source 6 may but does not necessarily include an infusor pump such as an expandable bladder-type pump, which increases in volume and pressure as fluid is introduced therein and subsequently contracts to force fluid out of the bladder during fluid delivery. Alternatively, the fluid source 6 may be a fluid container that provides fluid flow due to gravity such as, for example, by locating the fluid source at a height above the entry site into the patient, whereby the pressure head from the column of fluid above the entry site is sufficient to provide fluid flow to the patient. Other fluid sources may also be employed and are not limited to the above described sources.

In FIG. 1, the illustrated ambulatory fluid delivery system also includes a control system, generally indicated at 8, as shown in dashed lines. The control system 8 preferably includes a control module, generally indicated at 10, a flow valve, generally indicated at 12, a flow restrictor, generally indicated at 14, and a flow sensor, generally indicated at 16. As will be described in more detail later in another illustrated embodiment, portions of the control system 8, such as the control module 10, may be a durable, reusable device and the fluid flow path 4, valve 12, flow restrictor 14 and flow sensor 16 may be, in whole or in part, components of a disposable fluid circuit of flow set that is intended for one time use only.

In FIG. 1, the control module 10 may include an integrated circuit, microprocessor, printed circuit board and/or other control and/or memory devices such as shown and described in U.S. patent application Ser. No. 10/853,916, filed May 26, 2004, which is incorporated herein by reference. As will be described later, the control module 10 may be programmed to automatically perform for one or more fluid delivery therapies or flow profiles and/or it may be adapted to provide control of the fluid delivery by the user and/or patient. The control module 10 may also be adapted to store flow information for a selected flow profile, such as flow rate, pressure, temperature and/or other sensed information. Other variations are also possible.

The flow valve 12 is operatively associated with the fluid flow path 4 and is movable under the control of the control module between a first position, which corresponds to fluid flowing through the valve, and a second position, which corresponds to relatively limited or stopped fluid flow through the valve. Such first and second positions may, respectively, correspond to fully open and closed positions, although graduated valve positions and flow rates are also contemplated. As described in detail below, the actual flow rate to the patient may be based, at least in part, on some combination of the flow rates at each valve position and the respective time intervals of each position, as monitored and calculated by the control module.

As the system is illustrated in FIG. 1, the flow sensor 16 may be a pressure sensor for monitoring of the pressure through the fluid flow path 4, or for monitoring a feature or condition which is indicative of such pressure. It is contemplated that the present invention is not limited to a pressure sensor and that any sensor may be employed which sense other characteristics or flow conditions or information that is indicative of the fluid flow rate through the fluid flow path 4. However, in accordance with one aspect of the present invention, the flow sensor 16 preferably monitors the fluid pressure downstream of the flow valve 12 and more specifically, monitors the pressure difference in the fluid flow path 4 across the flow restrictor 14 via a first flow path 18 that communicates between the flow sensor 16 and the fluid flow path 4 at a location or junction that is located upstream of the flow restrictor 14 and a second flow path 20 that communicates between the flow sensor 16 and the fluid flow path 4 at a location or junction that is downstream of the flow restrictor 14. As described in more detail later, this arrangement allows the system to determine both fluid flow rate and actual fluid viscosity, providing a highly accurate system for administering medical fluid to a patient.

The control module 10 preferably includes a user or patient interface 24 for providing information and, optionally, for receiving input from the user or patient. The interface 24 may include an indicator module 26 such as a display screen for displaying flow-related information to the user and/or patient in graphical or numerical formats. Other indicators, such as color-coded lights or LEDs 28 may provide "at-a-glance" indications of other flow conditions or information. The interface 24 of the control module 10 may further include one or more actuators 30 to allow user programming or setting of a fluid therapy or profile and/or for limited patient control of the fluid delivery therapy as described later. The design of the interface 24 in FIG. 1 is shown for illustrative purposes only, as many other variations, modifications and alternatives are also possible which may include one or more of the features discussed above, alone and/or in combination with other features as discussed later.

Disposable System

Figure 2:
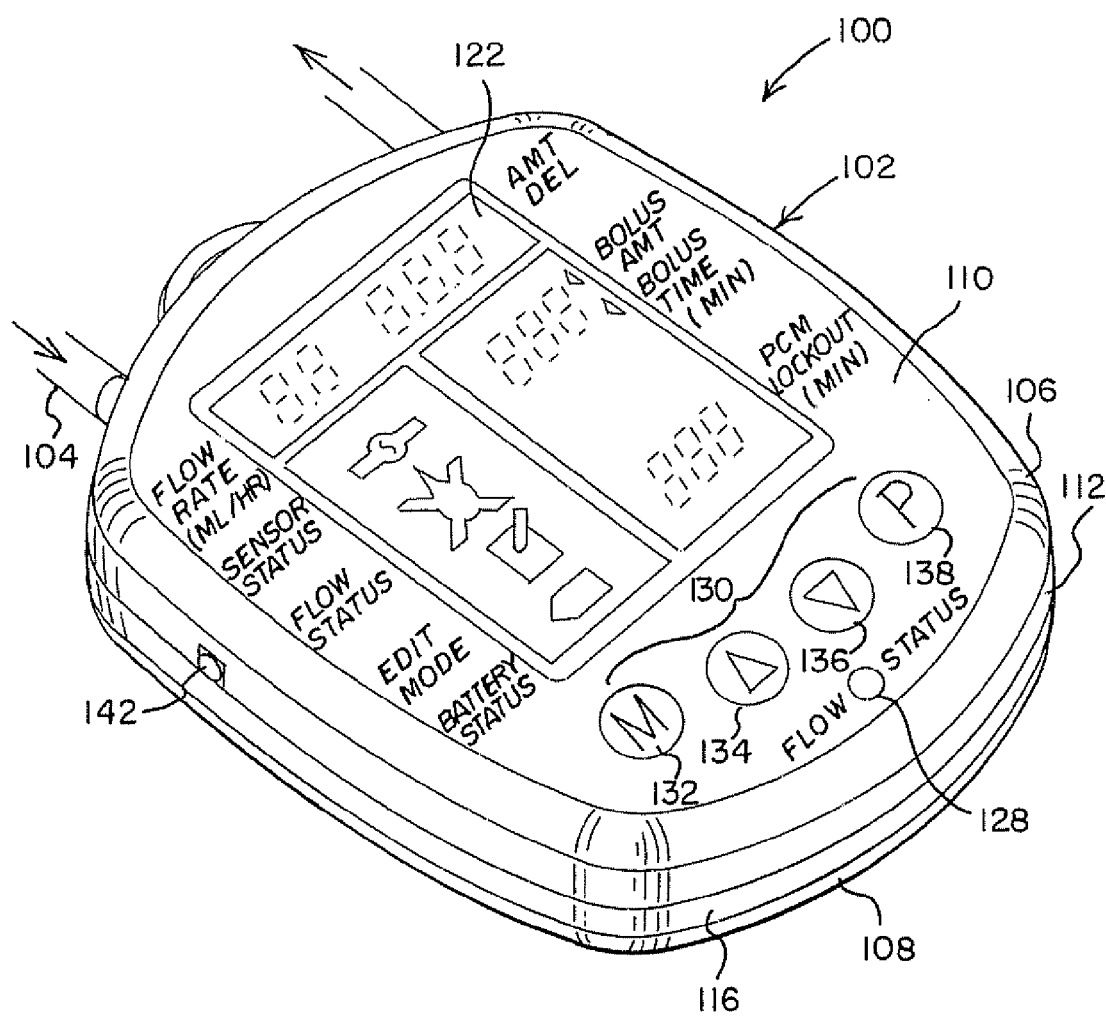
FIG. 2 is a perspective view of a second embodiment of an ambulatory fluid delivery system showing a controller and portions of a fluid flow path with the remaining portions of the fluid flow path and a fluid source not being shown.
Figure 3:
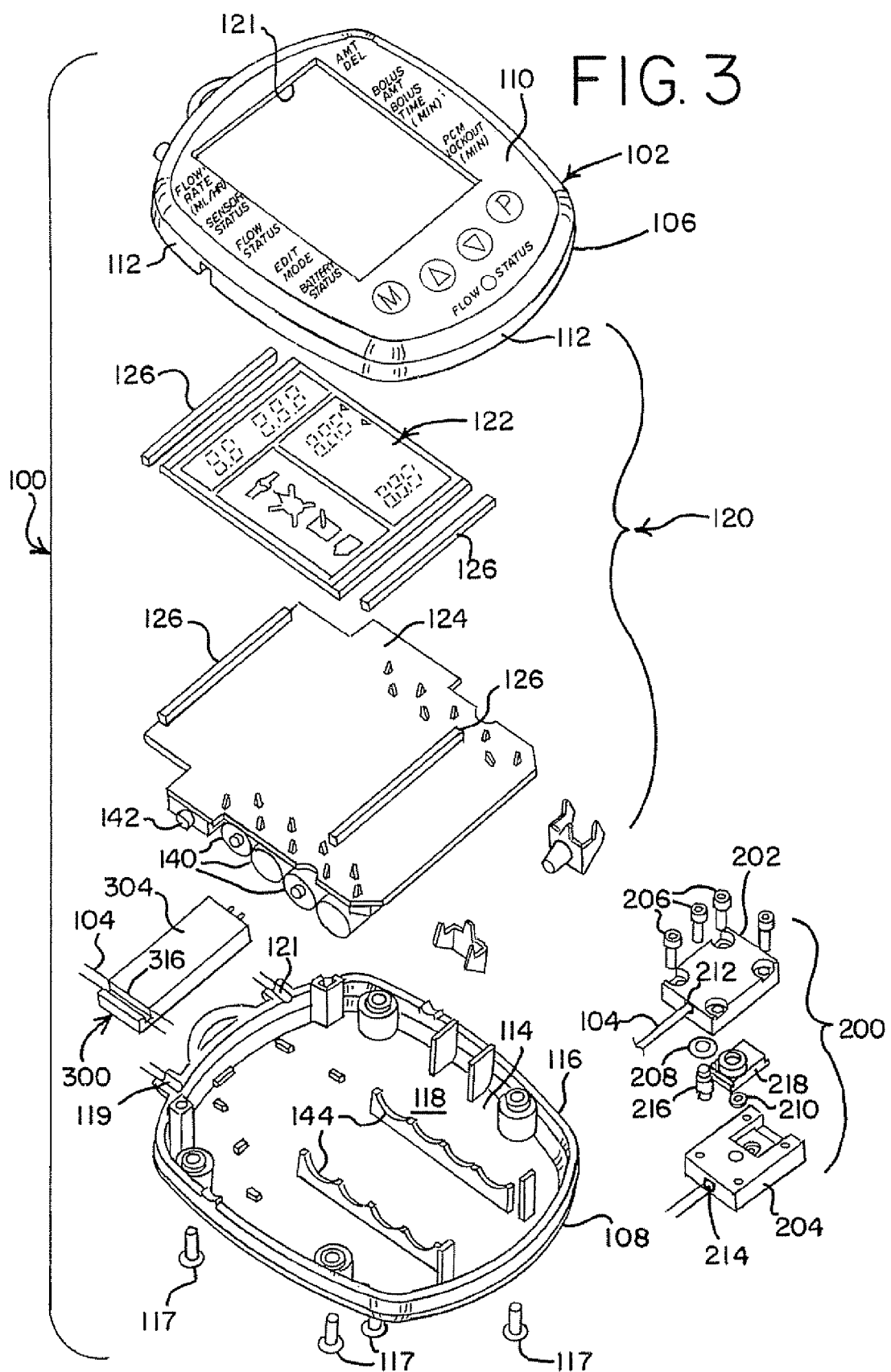
FIG. 3 is an exploded perspective view of the embodiment shown in FIG. 2.
Figure 4:
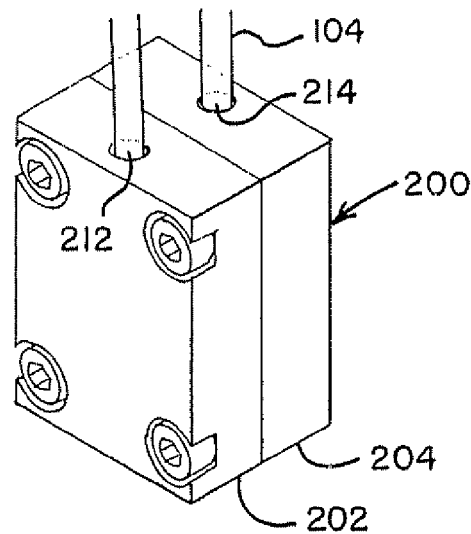
FIG. 4 is a perspective view of a flow sensor module which includes a flow sensor and a flow restrictor.
Figure 5:
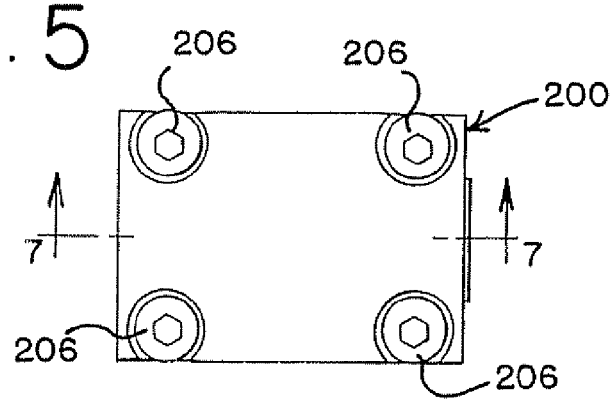
FIG. 5 is a front view of the flow sensor module in FIG. 4.
Figure 6:
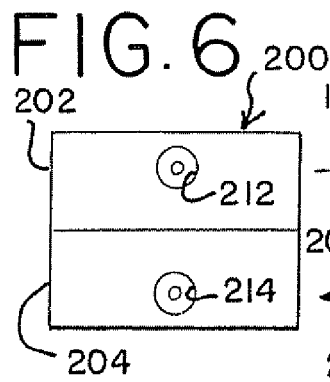
FIG. 6 is a side view of the flow sensor module in FIG. 4.

In accordance with a more specific embodiment of the present invention, FIGS. 2-3 illustrate a medical fluid delivery system, generally indicated at 100 which may be entirely disposable and is particularly suited for ambulatory administration of medical fluids. The flow system includes a controller, generally indicated at 102, that is associated with a fluid flow path 104, which is typically in the form of flexible plastic tubing. By "associated" it is meant that the controller 102 may be in direct fluid communication with the fluid passing through the flow path 104 and/or the controller 102 may indirectly act upon the fluid flow path for example, by acting on the tubing without being in direct fluid communication therewith or a combination of the above.

In FIGS. 2-3, the controller 102 includes a first or upper housing portion, generally indicated at 106, and a second or lower housing portion, generally indicated at 108. In FIGS. 2-3, the first housing portion may include a top or front surface 110 and a plurality of side edges 112. The second housing portion 108 may define a rear or bottom surface 114 and a plurality of side edges 116 such that the first and second housing portions 106, 108 define an internal compartment 118 and may be fastened together by suitable fasteners 117, or by bonding or other fastening means. The terms "first," "second," "upper," "lower," "front", "top," "rear," "bottom" and "side" as may be used here and elsewhere in this description with respect to other embodiments are merely used to aid description and are not intended to limit the present invention.

The first and second housing portions 106, 108 may provide for inlet and outlet ports, respectively, 119, 121 for the fluid flow path 104 or tubing associated therewith. In FIG. 3, the internal compartment 118 of the controller 102 may receive various components for controlling the flow of the ambulatory fluid delivery system including a control module, generally indicated at 120. In FIG. 3, the control module 120 generally includes a flow information indicator such as a display screen 122 and an integrated circuit and/or printed circuit board PCB 124, which may include an associated microprocessor e.g., a programmable microprocessor, to control the operation of the flow system.

In FIG. 3, the front surface 110 of the control system 102 may further include an opening 121 for receiving and displaying the flow information indicator 122 to the user and/or patient. As described in further detail herein, the front surface 110 may also include a flow status visual indicator 128 and a user/patient interface 130 with a plurality of actuators 132, 134, 136, 138 for controlling fluid flow, as described in further detail herein. The flow information indicator 122 and circuit 124 are preferably in electrical communication by various connectors 126 such as Zebra-strips or the like.

The controller 102 may include a power source 140, which may be internal such as by one or more batteries or, alternatively, the control system may be connected to an external power source by an appropriate electrical connection. The power source may be activated by a power control switch 142 so as to turn on and off the control system 102. Such power control switch 142 may be accessible through one of the first and/or second housing portions 106, 108 such as for example, in one of the sides 112, 116 although other locations are also possible. In FIG. 3, the internal power source 140 or batteries may be positioned in a side-by-side orientation using locators 144 and each may have a pair of respective electrical contacts 146 that provide for electrical connection to the control module 120 such as for connection to the circuit 124.

In FIG. 3, the control system also includes a flow sensor module, generally indicated at 200, and a flow control valve, generally indicated at 300, which are each associated with the fluid flow path 104 as described in more detail below. The control module 120 is preferably operatively associated with the flow sensor module 200 and the flow valve 300 to determine and control the actual flow rate through the fluid flow path.

As will be described in more detail later, the control module 120 may provide a determination of the actual flow rate in response to a sensed pressure difference measured by the flow sensor module 200 and, based on the determined actual flow rate, the control module 120 may control movement of the valve 300 between open and closed positions to change the actual flow rate, if necessary, by adjusting the on or off time of the valve. Alternatively, the control module 120 may operate to compare the actual flow rate to a desired flow rate and to change the actual flow rate to the desired flow rate based on a sensed difference between such flow rates. The desired flow rate may be preprogrammed by the user prior to the infusion procedure and/or adjusted by the user.

Flow Sensor Module

Turning to FIG. 3, the flow sensor module 200 (or also at 16 in FIG. 1) is preferably positioned downstream of the flow valve 300 (or at 12 in FIG. 1). As shown in detail in FIGS. 3-8, the flow sensor module 200 includes an upper housing portion 202, a lower housing portion 204 which may be fastened together by a plurality of fasteners 206, by bonding or other suitable techniques and/or include various sealing structures such as O-rings 208, gaskets 210 or the like for use in connection with sealing one or more portions of the flow control module.

In the illustrated embodiment, the medical fluid flows through the module, and for this purpose the module includes inlet and outlet ports 212, 214 located respectively in the upper and lower housing portions 202 and 204. As shown in FIG. 3, the tubing that defines the fluid flow path 104 may be attached to the inlet and outlet ports 212, 214 in a manner that achieves a fluid tight seal, such as mechanical attachment, ultrasonic, RF or solvent bonding or other connection arrangement.

Figure 7:
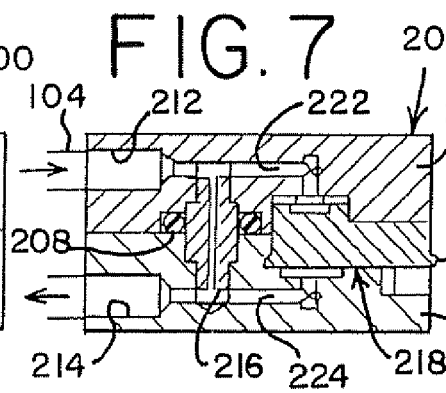
FIG. 7 is a cross sectional view along plane 7-7 of FIG. 5.
Figure 8:
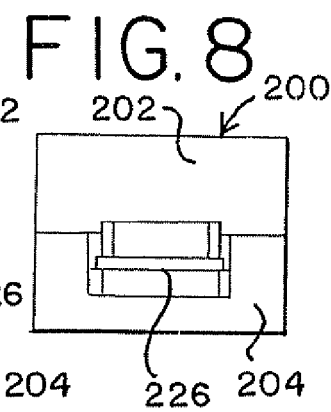
FIG. 8 is an opposite side view of the flow sensor module showing the side view opposite to FIG. 6.

As best seen in FIG. 7, the flow sensor module 200 includes a flow restrictor 216 and a differential pressure sensor 218. In FIG. 7, the flow restrictor 216 defines a flow restriction that is located between the inlet port 212 and the outlet port 214, and through which the medical fluid stream must pass. The flow restriction 216 may be of any desired form to define a flow region having a reduced cross-sectional size. It may comprise a simple orifice or an elongated member (as shown) of reduced inside diameter as compared to the fluid flow path upstream and downstream of the restriction. The flow restrictor 216 preferably has a fixed geometry, which may also assist in determining of the fluid viscosity, as described later.

The differential pressure sensor 218 may be a pressure sensor or transducer such as, for example, a pressure sensor that uses piezoresistive silicone die technology, such as manufactured by Measurement Specialties of Hampton, Va., USA or by other manufacturers, although other flow sensors may also be suitable for measuring other flow characteristics. To allow sensing of the pressure upstream and downstream of the flow restrictor, the flow module includes fluid flow paths 222 and 224 that communicate between the medical fluid flow path upstream and downstream of the restrictor 216 and the flow sensor 218. This arrangement allows the flow sensor 218 to measure the pressure differential between the upstream and downstream ends of the flow restrictor 216. It is noted that the flow sensor may directly measure such pressure differential as described above, or alternatively, such pressure differential may be measured indirectly such as by monitoring other information, which may be used to determine such pressure differential. The differential sensor 218 further includes a connector portion 226 for electrical connection between the flow sensor 218 and other portions of the controller 102 in FIG. 3. Such connector portion 226 may allow for electrical transmission of flow information that is sensed by the pressure sensor 218 (e.g., pressure drop across the restrictor) directly to the microprocessor or other circuitry.

With the knowledge of the pressure differential or "pressure drop" across the flow restriction, the rate of flow of fluid through the restriction may be calculated. As previously discussed above, the sensed pressure information from the flow sensor 16 in FIG. 1 or flow sensor module 200 in FIG. 3 may be communicated to the control module 10, 120 to determine the actual flow rate at a particular time instant or the relatively instantaneous actual flow rate. With the present invention, this is the real time or relatively instantaneous flow rate of medical fluid being administered to a patient through flow path 4 (in FIG. 1) or 104 (in FIG. 2). It is generally known that the relationship between the sensed pressure difference ($\Delta P$) and instantaneous flow rate (Q) may be generally represented by the following equation:

$$\Delta P = 128 \mu L Q / \pi d^4$$

Where $\mu$ represents fluid viscosity; L is the length of the reduced area defined by the flow restrictor; and d is the reduced diameter defined by the flow restrictor. The viscosity $\mu$ through the flow restrictor 14, 220 may be represented by the following equation:

$$\mu = B e^{A/T}$$

Where A and B are constants associated with the particular fluid; and T is the temperature of the fluid, which may be measured by an appropriate temperature sensor that may also be associated with the system. By combining the above two equations, the relationship between pressure and flow rate may also be represented by the following equation to allow for correction of the fluid viscosity due to temperature variation of such fluid:

$$\Delta P = K \mu Q = K B e^{A/T} Q = K_1 e^{A/T} Q$$

Where $K_1$ and A are constants that depend on the dimensions of the flow restrictor and the viscosity of fluid. This equation may be used to calculate a flow rate based on a sensed pressure difference, assuming all other values including the fluid viscosity are known. The viscosity may be known and stored in the memory of the control module and/or may be not known and the control module may also determine the viscosity, as described below, to calculate the actual flow rate.

Flow Valve

Referring back to FIG. 3, the flow valve 300 generally allows for fluid to be controlled through the fluid flow path 104. As shown in FIGS. 9-11, described below, the valve may be movable between a first position to allow fluid to flow through the fluid flow path 104 (as shown in FIG. 11) and a second position (as shown in FIGS. 9-10) to limit fluid flow through the fluid flow path. The terms "first" and "second" as they relate to the positions of the valve in FIGS. 9-11 are merely used to aid description of the relative movement that is permitted by the valve and such terms are not intended to limit the order or sequence in which such valve movement must occur.

In FIGS. 9-11, the flow valve 300 includes a housing having a base 302 and a cover 304, which is shown only in FIG. 3. The base 302 of the flow valve 300 includes a top surface 306, a bottom surface 308, a left side 310 and a right side 312. The cover 304 (not shown in FIGS. 9-11) may be attached to the base using suitable fasteners 314 or by bonding or other attachment means. The flow valve 300 preferably includes a channel or slot 316 for receiving the plastic tubing forming the fluid flow path 104. Although the flow valve 300 in FIGS. 9-11 is shown as acting upon or pinching the external surface of tubing which defines the fluid flow path 104, other valve constructions are also possible. For example, the fluid flow path 104 itself may be defined in part by the channel 316 for fluid flow directly therethrough.

As illustrated in FIGS. 9-11, the flow valve 300 also includes a flow control member 318, which is pivotably attached to the base 302 via pivot 320 such that the flow control member 318 is pivotably movable relative to the pivot 320. The flow control member 318 includes first and second arms, respectively, 322 and 324. The first arm 322 generally extends laterally from the pivot 320 toward an opening 326 in the wall defining channel 316, and the second arm 324 generally extends downwardly from the pivot 320 to cooperate with a biasing means. More specifically, the first arm 322 includes a first end 328 and the second arm 324 includes a second end 330. The first arm 322 includes a groove 332 positioned proximal to the first end 328 and an extension 334. The extension 334 generally extends upwardly in a direction toward the channel 316 and through the opening 326 formed in such channel.

The flow valve 300 further includes a biasing member such as a spring 336. The biasing member 336 includes a first end 338 attached to a fixed member or post 342, and a second end 340 is secured within an aperture 344 in the second arm 324 of the flow control member 318. The biasing spring 336 preferably normally is in tension and exerts a pulling flow control force on arm 324, biasing the member to the position shown in FIG. 10, where the extension 334 pinches the tubing 104 closed, so that the valve is normally closed when not activated. It is noted that the valve may be normally biased to a closed or flow limiting position to avoid free fluid flow to the patient, although other constructions are possible such as a biasing member that normally positions the valve in an open position.

To open flow through the flow path, the flow valve 300 also includes an actuator 346 which is illustrated in a general V-shape. The activator includes first and second legs or ends 348 and 350, as shown in FIGS. 10-11, and an intermediate portion 352 which is preferably received within the groove 332. The first and second ends 348 and 350 are received by respective conductive sockets 354 and 356 in the base 302.

The actuator 346 is preferably made of a shape memory material. By "shape memory material" it is meant that the actuator may be adapted, by application or removal of energy (such as a change in temperature) to change in shape, dimension, orientation or other condition so as to cause movement of the flow control member 318. As illustrated, the actuator 346 is in the form of a wire and made of a shape memory material to change in length upon a change in temperature. One example of a shape memory material may include an alloy of nickel and titanium, although other shape memory materials are also possible.

In FIGS. 9-11, the application of electrical current and/or heat to the actuator 346 causes the shape memory material to contract, causing the valve to open and remain open so long as electrical current and/or heat is being applied to the actuator or, if electrical current is temporarily shut off as described further below, so long as the temperature of the actuator is sufficient to keep its shortened length. To heat to the actuator 346, the conductive sockets 354, 356 are connected to an electrical voltage source, which upon activation cause electrical current to flow through the wire to cause resistive heating in the wire, and, thereby increasing the temperature of the actuator 346. Of course, the wire may be heated by other means such as by an external heater in contact with the shape memory wire. Preferably, when heated, the actuator 346 changes or shortens along all or a substantial portion of its length. For example, the actuator 346 may shorten or contract in length by about 4% when heated either externally or internally with an electrical current. When the electrical current is stopped, the actuator cools and expands or lengthens, returning to its prior length. Of course, other means to change the temperature may also be used. Alternatively, the movement of the actuator may be used other than by change in temperature including other means which employ mechanical, magnetic, electrical, pneumatic or others and/or a combination thereof.

FIGS. 10-11 illustrate movement of the valve between the first and second positions. In FIG. 10, due to biasing force of spring 336, the flow control member 318 is pivoted counterclockwise, with the extension 334 extending through the opening 326 in the channel 316 to engage the external surface of the tubing that forms the fluid flow path 104 and pinching or clamping the tubing of the fluid flow path 104 between the extension 334 and a surface of the channel 316 that is opposed to such opening 326. The inner diameter of the fluid flow path 104 is constricted, limited and/or closed to fluid flow through such tubing. As illustrated, the flow is completely closed in the position shown in FIG. 10, although graduated closure or restriction is also possible. Heating of the actuator 346 such as by passing current through the actuator preferably causes the arm 322 to pivot clockwise from the position shown in FIG. 10 to the position shown in FIG. 11, where extension 334 is moved away from the fluid flow path 104 to a position where it is essentially located out of the channel 316 in FIG. 11, thereby opening the tubing to allow fluid flow through flow path 104.

The illustrated valve 300 further includes two normally spaced-apart conductive contacts 358 and 360 each having at least one end disposed so that movement of the valve, i.e., the flow control member 318 or, more specifically, its end 330, pushes the contacts 358, 360 into conductive engagement with each other. The contacts 358, 360 may provide an indication of the on and/or off position of the valve and/or communicate a signal, such as an electrical current, that is indicative of such position to assist control of the valve by the control module 10, 120 and/or to provide a more precise control of valve movement for adjustment to the actual flow rate, as described further below. For example, the conductive engagement between the contacts 358, 360 may be communicated to the control module to indicate that the valve is in an open position. Other means, electrical, mechanical or other, may be employed for determining the valve position and/or for communicating such information to other parts of the system.

The contacts 358, 360 may also assist in limiting current that is required to keep the valve in an open position. In FIGS. 9-11, the contacts 358, 360 generally comprise part of a cut-off switch that normally allows electrical current to be supplied to the actuator 346, via sockets 354, 356, thereby increasing the temperature of and causing shortening of the actuator or wire 346 to move the valve to the open position. To avoid overheating of the actuator 346, the conductive engagement between the contacts 358, 360 may initiate the control module to shut off the current that is supplied to the sockets 354, 356 to heat the actuator 346. As the actuator 346 begins to cool, the end 330 of the flow control member 318 moves counterclockwise to disengage the contacts 358, 360 from one another, which allows the control module to supply electrical current to the sockets 354, 356 in order to keep the valve in the open position. By way of example and not limitation, the cut-off switch may move between on and off positions or "flutter" at a rate of about 100 times per second, although other rates are also possible. The cut-off switch may avoid overheating of the actuator 346 while still essentially keeping the valve in the first or open position. Operation of the cut-off switch may also assist in limiting the power requirements for valve movement. Other variations and modifications are also possible.

Among the benefits provided by the actuator 346 in FIGS. 9-11, such actuator provides a convenient control mechanism for opening the valve, closing the valve and/or limiting flow through the valve. The actuator 346 may provide for valve movement with relatively low power requirements and with fewer mechanical parts than may otherwise be required, with consequent ease of assembly. The shape memory material of the actuator 346 provides a relatively reliable material that may be repeatedly used, by heating and cooling, for valve movement without significant variation and/or deterioration to the shape and configuration of such material by such repeated heating and cooling. Further, the actuator 346 may be made of material that is relatively lightweight for an ambulatory system.

FIGS. 12-14 show an alternate flow valve 362 construction. The illustrated valve in FIGS. 12-14 includes a housing having a base 364 with the cover shown removed, similar to FIGS. 9-11. The flow valve 362 similarly includes a channel or slot 366 for receiving the plastic tubing forming the fluid flow path 104 and a flow control member 368. A longitudinal extension 370 of the flow control member 368 is movable through an opening formed in the wall of the channel 366 to allow for the valve to move between a first or open position and a second or flow limiting position. A groove 372 is formed in the flow control member 368 proximal to the extension and receives an actuator 374 that includes two ends that extend toward the bottom of the flow control member 368 to conductive contacts 376 (as seen in FIGS. 13-14). A biasing member 378 such as a spring at the bottom of the flow control member 368 normally biases the flow control member into the position shown in FIGS. 12-13, in which the valve is shown in the second position.

The illustrated valve in FIG. 12 also includes a latching member 380 having a lateral extension 382, which preferably engages a notch 384 formed in the flow control member 368 in the position shown in FIG. 14. A separate biasing member 386, which may be a spring, (as shown in FIG. 13-14) normally biases the latching member 380 laterally towards the flow control member 368 (e.g., to the right in FIGS. 12-14) in each of FIGS. 12-14. The latching member 380 is also connected to a control member 388, which is preferably made of a shape memory material and may be a wire, such as shown in FIGS. 12-14. Each end of the wire 388 may be connected to conductive contacts 390 for connection to an electrical current supply source.

FIGS. 13-14 illustrate movement of the valve between first and second positions. In FIG. 13, the biasing force of the spring 378 biases the flow control member 368 upwards, with the extension 370 extending through the opening the channel 366 to limit flow through the fluid flow path 104. Heating of the actuator 374, such as by passing an electrical current through the actuator 374, causes the actuator or wire 374 to shorten and the flow control member 368 slidably moves downward, compressing the spring 378, as shown in FIG. 14. The extension 370 moves away from the fluid flow path 104 to a position where it is essentially out of the channel 366 to allow flow through the valve 362. As the flow control member 368 slidably moves downward, the extension 382 of the latching member 380, which is biased laterally toward the flow control member 368 by the spring 386, engages the notch 384. The latching member 380 may be disengaged from the notch 384 by heating, and thus shortening, of the control member or wire 388, which moves the latching member away from the notch to the position shown in FIG. 13. The latching member 380 may be helpful to assist in maintaining the valve position in FIG. 14 with limited power requirements or without requiring electrical current to be supplied to the contacts 376 to maintain such position.

In FIGS. 12-14, the illustrated valve 362 also includes two pairs of spaced apart conductive contacts, respectively at 392 and 394. The first pair of conductive contacts 392 provides a cut-off switch to the actuator 374 to avoid overheating of the actuator or wire 374, similar to as described above in FIGS. 9-11. For example, an arm 396 extends downwardly from the flow control member 368 to push the contacts 392 into engagement with one another upon downward movement of the flow control member 368 so that the control module may shut off current to the actuator 374. Upon cooling of the actuator 374 and upward movement of the arm 396, the contacts 392 disengage and the control module may turn on the current to the actuator 374 to keep the valve in the position shown in FIG. 14.

In FIGS. 12-14, the second pair of conductive contacts 394 provides a cut-off switch to the control member 388 to avoid overheating of the control member or wire 388. To move the latching member 380 away from the flow control member 368, the control member 388 is heated, causing shortening of the control member 388 or wire and compression of the biasing member 386. In FIG. 13, an edge or surface of the latching member 380 pushes the conductive contacts 394 into engagement to allow for the control module to shut off current to the control member 388. Upon cooling of the control member 388, the latching member 380 moves away from the contacts 394, which disengage from one another, to allow for the control module to supply current to the control member 388. As previously described above with other cut-off switches, the electrical current to the control member 388 may alternatively be switched on and off or "flutter" in response to control by the control module so as to conserve power and to limit overheating of the control member 388. Preferably, such cut-off switch is operated on and off until the flow control member 368 moves to the position shown in FIG. 13, in which the extension 382 is biased against the flow control member 368 just below the notch 384. Other valve constructions are also possible.

FIG. 15 shows another alternate flow valve 400 construction. That valve includes a housing 402, a channel or slot 404 for receiving at least a portion of the tubing forming the fluid flow path 406. The valve 400 includes a flow control member 408, a biasing member or compressed spring 410 and an actuator 412. The actuator 412 provides for movement of the valve between a first position that allows fluid flow through the fluid flow path 406 and a second position which limits or completely stops flow through the fluid flow path 406, with only the second position being shown in FIG. 15. In accordance with the embodiments shown in FIGS. 9-14, the actuator 412 in FIG. 15 may be a wire although other structures are also possible. The actuator 412 may include first and second ends 414 and 416 and an intermediate portion positioned between such ends, which portion engages the flow control member 408 for valve movement. More specifically, the flow control member 408 may be attached to one end 418 of the biasing member, i.e., compressed spring 410, with the other end 420 of the spring preferably being fixed to the housing 402 so that the flow control member 408 is biased by the compressed spring 410 through a channel opening 422 for engagement with the tubing defining the fluid flow path 406 to limit fluid flow therethrough.

As previously described, the actuator 412 is preferably made of a shape memory material. The actuator 412 may be heated such as to change its length, although other constructions are also possible for activation of the valve. The first and second ends 414 and 416 of the actuator may be electrically connected to an electrical energy source which, upon direction from the control system, provides an electrical current to the actuator, causing resistance heating and shortening or contraction of the actuator 412. This shortening causes further compression of spring 410 and movement of the flow control member 408 away from the tubing defining flow path 406 thereby opening the flow path to increased fluid flow. By varying the current through the actuator and the amount of resistance heating, the flow path is either opened or closed.

In FIG. 16, a further modification of a valve 450 is shown. Valve 450 includes a housing 452 and also defines a channel 454 that is associated with plastic tubing defining a fluid flow path 456. In FIG. 16, an opening 458 is provided in the wall of channel 454. A flow control member 460 is located for slidable movement so as to engage the tubing defining fluid flow path 456 through the opening 458. In FIG. 16, the valve 450 is disposed in a first position in which fluid flow is allowed to flow through the fluid flow path 456. Although not shown, the valve may be slidably moved to a second position in which the flow control member 460 compresses or pinches the flow path tubing to limit fluid flow through the fluid flow path 456. One or more guides 462 may assist in constraining the flow control member 460 for slidable movement toward and away from the flow path tubing.

As shown in FIG. 16, the movement of the flow control member is controlled by a cam 464 which is pivotably movable relative to a pivot 466. The cam 464 includes first and second grooves 468 and 470, which are located on opposed sides of the pivot 466. The valve 450 includes first and second actuators 472 and 474, which each respectively have first ends 476 and 478, second ends 480 and 482 and intermediate portions 484 and 486. Each intermediate portion 484 and 486 is received by one of the respective grooves 236 and 238. Movement of the cam 464, and thus the flow control member 460, is controlled by first and second actuators 472, 474, which may each be made of a shape memory material, such as described above, which each may be heated to cause valve movement corresponding to a different position.

For example, heating of the actuator 472 may cause a shortened length, which results in pivotable movement of the cam 464 in a counterclockwise direction. Such movement causes the cam 464 into engagement with the flow control member 460, and moves the control member to limit flow through the fluid flow path 456. For this operation, it may be expected that actuator 474 is not heated, not heated as much as actuator 472 or actually cooled to allow pivoting of the cam 464. In contrast, heating of the other actuator 474 to shorten the length thereof (coupled with the absence of heating, less heating or cooling of actuator 472) may cause clockwise pivotable movement of the cam 464 such that the cam moves out of engagement with the flow control member 460.

The flow control member 460 in this embodiment may be normally biased to a position out of engagement with the tubing defining fluid flow path 456 to allow fluid flow therethrough upon such clockwise pivotable movement of the cam 464. For example, the valve 450 may include a magnet which provides a magnetic force that normally holds the flow control member 460 in the open valve flow position and the cam 464 may be pivotably movable to oppose a magnetic force so as to move the valve to a restricted flow position. Alternatively, the magnetic force may be arranged to hold the flow control member in a restricted flow position. Other valve constructions are also possible.

Figure 17:
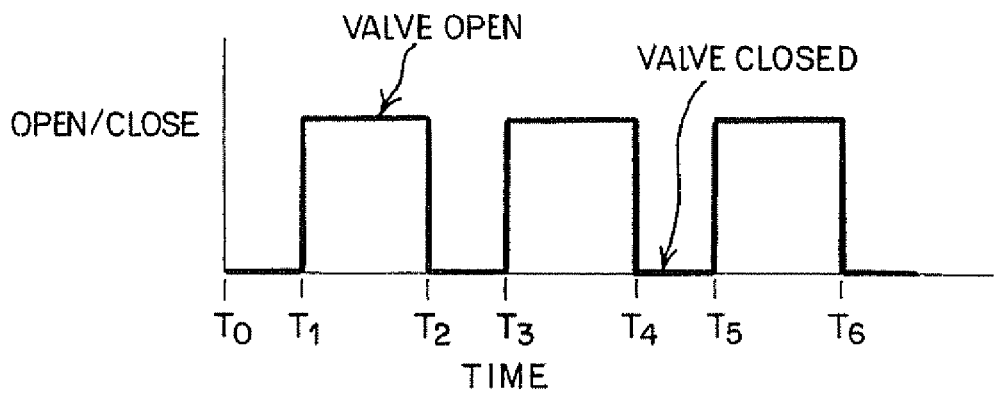
FIG. 17 is a graph showing the open and closed positions of the valve over time.

The illustrated valves in FIGS. 9-16 move between fully open and fully closed positions to control the flow of fluid to the patent. By way of example and not limitation, FIG. 17 illustrates the relative movement of the valve between open and closed positions over a selected time interval for a selected fluid delivery system. In FIG. 17, the open position of the valve may correspond to a maximum flow rate and the closed position of the valve may correspond to a substantially zero flow rate. Alternatively, the open and closed positions of the valve may correspond to other flow rates. By way of example and not limitation, instead of a closed position, the valve may be positioned to allow a limited flow rate. In FIG. 17, the flow valve may be closed for a time interval from a time $T_0$ a time $T_1$ and may be open from a time $T_1$ to a time $T_2$, which completes a first cycle of valve movement between the closed and open positions over the entire time interval of time $T_0$ to $T_2$. FIG. 17 shows three cycles of the valve alternating between closed and open positions with the closed position occurring at time intervals $T_0$ to $T_1$, $T_2$ to $T_3$ and $T_4$ to $T_5$ and the open position occurring at alternating time intervals $T_1$ to $T_2$, $T_3$ to $T_4$ and $T_5$ to $T_6$. It is contemplated that each time interval may be similar to or different from any other and such interval may depend on the actual flow rate that is desired through the fluid flow path.

Figure 18:
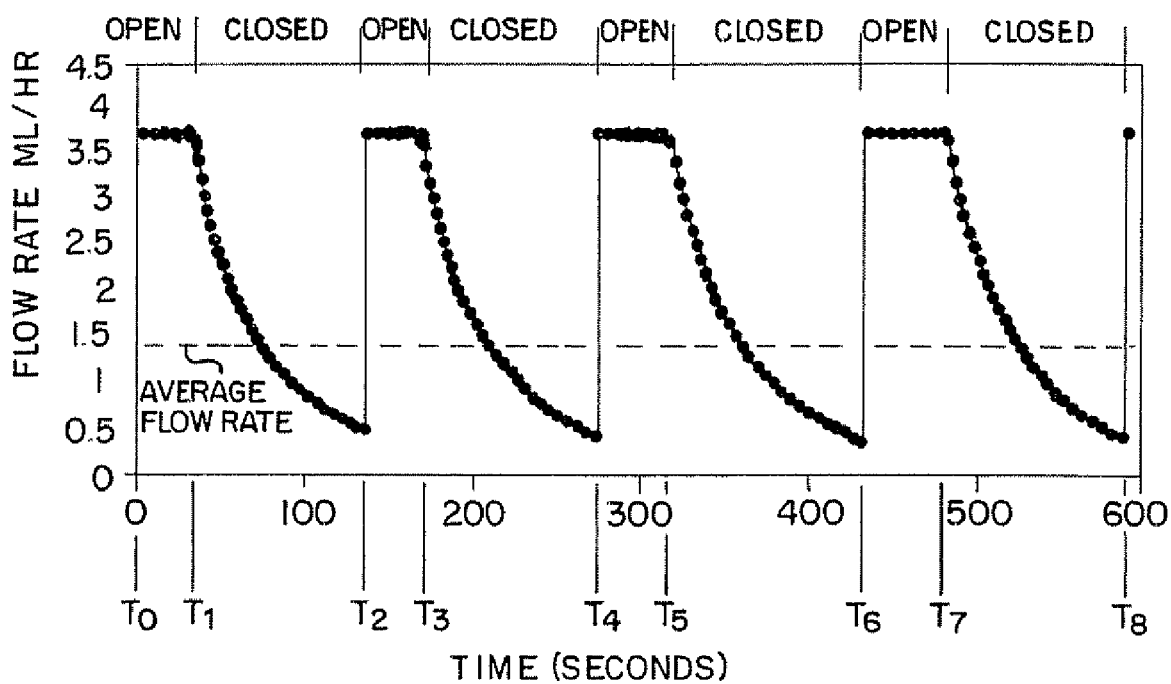
FIG. 18 is a graph showing flow rate (in milliliters per hour) versus time (in seconds) in accordance with the use of the present invention.

FIG. 18 shows examples of the real time or instantaneous fluid flow rates through the fluid flow path at a location that is just downstream of the valve over a selected time interval of alternating valve open and closed positions, which flow rates may be calculated, for example, by employing the sensed pressure difference at a particular time instant. As indicated, the valve may be opened at time intervals $T_0$ to $T_1$, $T_2$ to $T_3$, $T_4$ to $T_5$ and $T_6$ to $T_7$ and correspond to a relative maximum flow rate. The valve may be closed at time intervals $T_1$ to $T_2$, $T_3$ to $T_4$, $T_5$ to $T_6$ and $T_7$ to $T_8$ and correspond to a flow rate that decreases exponentially from the instant that the valve is closed until the flow rate reaches essentially zero or the value is opened again. In particular, FIG. 18 shows a flow profile in which the valve is in an open position beginning at time $T_0$ to time $T_1$ at about 33 seconds and has an instantaneous flow rate of approximately 3.75 milliliters per hour (mL/hr). FIG. 18 shows the valve in a closed position from time $T_1$ to time $T_2$ at about 133 seconds and having a fluid flow curve that exponentially decreases over such time period from 3.75 mL/hr to about 0.5 mL/hr or less. At the end of the first cycle of movement of the valve at time $T_2$, the movement of the valve may be repeated for a second cycle. For example, at time $T_2$, the valve is in the open position in which the flow rate instantaneously increases to about 3.75 mL/hr a subsequent later time interval from time $T_2$ to time $T_3$ and further shows the closed position for another later time period from time $T_3$ to time $T_4$. FIG. 15 also shows subsequent cycles of the valve movement between open and closed positions for a total of four cycles in which the valve is opened and closed. As noted above, the time intervals for the open and closed positions of the valve may be varied for each cycle and for any number of cycles.

Although the instantaneous flow rates just downstream of the valve are indicated in FIG. 18, the actual flow rate that is delivered to the patient, as may be indicated by the dashed horizontal line in FIG. 18, is a combination of these flow rates. Such actual flow rate that is delivered to the patient may comprise an average or some other combination of the instantaneous flow rates during a selected time period of valve movement. Preferably, the actual flow rate that is delivered to the patient may be determined based on the total area of the flow curve as integrated over the appropriate time interval. Such integration may be iteratively performed by the microprocessor throughout the fluid infusion profile to determine the actual fluid flow rate through the fluid flow path, for example, in accordance with a preset time increment, such as about every 2-3 seconds although other increments are also possible.

For example, the actual flow rate through the fluid flow path for the first cycle of valve open and closed positions may be based a determination of the total area beneath of the flow curve in FIG. 18 integrated over a time interval from time $T_0$ to time $T_2$. Such flow curve includes the initial flow rate of the valve in the open position from time $T_0$ to $T_1$ and the decreasing flow rate curve that occurs over time interval $T_1$ to $T_2$. Other actual flow rates may be determined for other selected time intervals.

The actual flow rate may be varied by adjusting the time intervals of the valve open and closed positions, i.e., the pulse width in FIGS. 17-18. For example, if the actual flow rate to the patient is too low or too high, then the system may be adapted to adjust the flow rate upwardly or downwardly. If the flow rate is too low, then the system may automatically increase the actual flow rate by decreasing the time interval that the valve is closed, i.e., $T_1$ to $T_2$, $T_3$ to $T_4$, $T_5$ to $T_6$ and $T_7$ to $T_8$ in FIG. 18 and/or decreasing the frequency of such intervals. Alternately, it is possible to increase the flow rate by increasing the time intervals that the valve remains open, i.e., $T_0$ to $T_1$, $T_2$ to $T_3$, $T_4$ to $T_5$ and $T_6$ to $T_7$ and/or increasing the frequency of the time intervals that the valve remains open. If the actual flow rate to the patient is too high, then the system may be adapted to decrease the flow rate downwardly by increasing the time interval between that the valve remains closed and/or increasing the frequency of the time intervals that the valve is closed, or, alternatively, by decreasing the time interval or frequency that the valve is open. This adjustment may be performed continuously, at selected time intervals, after a selected user or patient activated change and/or a combination thereof. For example, this adjustment may be performed in response to the integrated actual fluid flow rate if the integrated actual fluid flow rate differs from the desired fluid flow rate.

The present invention further provides several benefits for controlling the fluid flow in fluid delivery systems, such as an ambulatory system. Among such benefits, the present invention allows for real-time adjustment of the actual fluid flow rate that is delivered to the patient through the fluid flow path and/or for changing of such actual fluid flow rate in response to a difference between the actual fluid flow rate and a desired fluid flow rate for a selected flow profile. Although determination of the actual fluid flow rate will described with respect to the systems shown and described in FIGS. 1 and 3, it is possible for any of the embodiments described herein to perform such determination.

In FIGS. 1 and 3, the control module 10, 120 may be programmed with suitable software that operates a feedback control loop to control and/or adjust the actual flow rate in the flow fluid path. As previously described, the control module 10, 120 determines or calculates the actual flow rate in the fluid flow path 4, 104, such as based, in part, on the sensed pressure information by the flow sensor 16, 200, and on the pulse width modulation of the value (e.g., the length of the time intervals of the valve at the first or open position and the second or closed position) over a selected time interval. Based on the measured actual flow rate, the control module 10, 120 may adjust the actual flow rate, such as by controlling the on and off movement of the valve, to increase or decrease the flow rate of fluid received by the patient.

Another benefit of the present invention allows may provide for determining a difference between the actual fluid flow rate and a desired flow rate. The desired fluid flow rate may be a flow rate as prescribed by the doctor, surgeon or other medical professional of a particular fluid for the patient. It is possible that the desired fluid flow rate may be programmed into the control module 10 prior to the fluid delivery therapy as part of a preset flow profile and/or be the result of a patient-activated change during a particular fluid delivery therapy.

For example, the actual fluid flow rate is determined by one of the systems in FIGS. 1-3. The flow sensor provides flow information such as a sensed pressure difference that is communicated to the control module 10, 102 which, in turn, determines an actual flow rate. The control module 10, 102 may include at least one flow control signal generator such as a logic operator, input/output device or other control device generates a first flow control signal that is responsive to a measured actual flow rate. The control module 10, 102 preferably compares the actual flow rate to the desired flow rate. If the actual flow rate is different from the desired fluid flow rate, then the system components such as the microprocessor or other circuit components may automatically adjust the actual fluid flow rate, by increasing or decreasing the valve open or valve closed position time (thus increasing or decreasing the actual flow rate) to achieve the desired fluid flow rate. The system components may be adapted to generate a second flow control signal in response to a sensed difference between the actual and desired flow rates that corresponds to the appropriate adjustment in the valve movement. Other variations or modifications are also possible for adjustments to the actual flow rate.

The control system 8 may change the valve movement in response to flow control signals generated by the control module 10 to alter the flow rate curve. The actual flow rate may be increased or decreased as appropriate depending on whether the actual flow rate is less than or greater than the desired flow rate. The actual flow rate may be monitored continuously or over a selected time period after such change so as to determine whether the change in the actual flow rate is sufficient to provide the desired flow rate.

The comparison between the actual flow rate and the desired flow rate may occur continuously throughout the fluid delivery therapy or may be performed at predetermined intervals. The system is preferably adapted to automatically compare the actual flow rate to a desired flow rate and, based on any difference or a difference outside of acceptable tolerances, to automatically increase or decrease the actual flow rate (by adjusting valve pulse width) so as to achieve a desired flow rate.

The control system 8 also may operate valve movement in response to flow control signals generated by the control module 10 such as to monitor for abnormalities in the fluid flow. Examples of such abnormalities include unexpected occlusions or blockages in the flow path, valve malfunctions, an empty fluid source and/or other flow disrupting conditions. By way of example, the system may monitor fluid flow in the flow path during operation by forcing the valve to a closed position for a sufficient time period so that the system recognizes an occlusion or "no flow" condition through the flow path and the pressure drop across the flow restrictor is about zero. The valve may be subsequently opened and the pressure drop across the flow restrictor may be measured. If the pressure drop across the flow restrictor remains unchanged after opening the valve, then the system may indicate an occlusion or other "no flow" condition in the flow path such as due to a blockage in the flow path, valve malfunction, an empty fluid source and/or other factors. In such example, the control system preferably differentiates from "normal" occlusions in the flow path that result from the valve closed position, as shown and described at $T_0$ to $T_1$, $T_2$ to $T_3$ and $T_4$ to $T_5$ in FIG. 17 or at $T_1$ to $T_2$, $T_3$ to $T_4$, $T_5$ to $T_6$ and $T_7$ to $T_8$ in FIG. 18, during normal operation of the valve to provide the actual flow rate. To monitor for abnormal occlusions or blockages, the system may, for example, employ a longer time interval for the valve closed position. Other variations, modifications and alternatives are also possible. Other procedures for measuring the actual flow rate may also be employed.

Viscosity Determination

The present invention may further beneficially provide for determining the fluid viscosity of the fluid that is being delivered to the patient. The determination of the fluid viscosity may be helpful to the determination of the actual flow rate so as to provide a more accurate actual flow rate of a particular medication, to accommodate for changes in viscosity due to temperature changes and/or to avoid having to program different viscosities of various fluids into the system. The control system 8 may be automatically programmed to determine the viscosity and/or determine viscosity at one or more selected time intervals prior to or during the flow profile. Among further benefits of the present invention, the viscosity that is determined by the control system 8 may be compared to the viscosity of the fluid that is identified by the health professional, pharmacist or other user at a selected time such as prior to infusing such fluid to the patient. This comparison may be useful to avoid misidentification of the fluid that is infused to the patient and control system 8 may further generate an alarm to the user when the determined viscosity is substantially dissimilar to such user-identified viscosity to avoid infusing such fluid to the patient.

In accordance with this aspect of the present invention, the control system 8 determines viscosity based on a measured decay time of a pressure drop at a selected location in the fluid flow path 4. Although such determination of viscosity will be described for the embodiment of FIG. 1, any of the embodiments discussed herein may be employed for determining viscosity.

As shown in FIG. 1, the control module 10 is operatively associated with the flow sensor 16 for sensing fluid pressure within the fluid flow path 4 at a selected location upstream of the flow restrictor 14. The flow sensor senses the fluid pressure through the flow sensing path 18, which communicates with the fluid flow path 4 upstream of the flow restrictor 14. (Also see flow sensing path 222 upstream of restrictor 216 in FIG. 7). The control module 10 senses a first pressure at a first time period, when the valve is in the first or open position. Then the valve 12 is moved to a closed position, and a second pressure (at the same location) is sensed at a second time period after the pressure has exponentially decreased to a relatively lower pressure than the first pressure.

The graph of FIG. 19 shows the differential pressure sensed by the flow sensor at the selected locations between the upstream and downstream of the restrictor as the valve is moved between a first and second position at selected time intervals. More specifically, the pressure curve is highest when the valve is at the first or opened position (such as between T and $T_2$) and decreases as the value is moved to the second or closed position. In FIG. 19, the time intervals $T_0$ to $T_1$, $T_2$ to $T_3$, $T_4$ to $T_5$ and $T_6$ to $T_7$ generally correspond to the valve being closed and the time intervals $T_1$ to $T_2$, $T_3$ to $T_4$, $T_5$ to $T_6$ and $T_7$ to $T_8$ generally correspond to the valve being open. At time interval $T_0$ to $T_1$, the valve is in the closed position, and the fluid pressure upstream of the restrictor and downstream of the valve is about 0 psi. At time $T_1$, the valve is opened and the pressure nearly instantaneously increases to about 7 psi and remains there for a time interval $T_1$ to $T_2$. At time $T_2$, the valve is closed and the pressure at the sensed location exponentially decreases over a time interval from $T_2$ to $T_3$ from 7 psi to about 0 psi.

The control module 10 preferably determines a time interval ($\Delta t$) between the first and second pressure sensing events, such as measured at times $T_2$ and $T_n$, where n may be any other time instance, and determines the pressure change or drop ($\Delta P$) that occurred during such time interval ($\Delta t$). Such time interval ($\Delta t$) may also be referred to as the decay time ($\Delta t_{decay}$) and is preferably automatically measured by the control module 10 or integrated circuit components such as by the microprocessor, which may be programmed to automatically measure such decay time. The control module 10 may be programmed to measure the decay time for a predetermined pressure drop to occur. Alternatively, the control module 10 may be programmed to measure a pressure drop that is associated with a predetermined time interval ($\Delta t$). It is noted that the pressure drop that occurs in the fluid flow path after closing of the valve generally decreases exponentially according to the following equation:

$$P = Ae^{-Bt}$$

Where P is the instantaneous pressure; t is the instantaneous time; and A and B are constants that depend on the fluid viscosity, the dimensions of the flow restrictor and the section of tubing downstream of the valve.

The pressure ratio between two pressure sensing events, $P_1$ and $P_2$, which are respectively sensed at two time instants, $t_1$ and $t_2$, may be represented by the following equations:

$$P_1/P_2 = e^{-Bt_1}/e^{-Bt_2}$$

$$\ln(P_1/P_2) = -B(t_1 - t_2)$$

$$\Delta t = t_1 - t_2 = -(\ln P_1 - \ln P_2)/B = B_1(\ln P_1 - \ln P_2)$$

Where $P_1$ is the pressure at a first time $t_1$; $P_2$ is the pressure at a second time $t_2$; $t_1$ is the first time; $t_2$ is the second time; $\Delta t$ is the decay time or time interval from the first time $t_1$ to second time $t_2$ for the pressure to drop from $P_1$ to $P_2$; Where $B_1$ ($= -1/B$) is a constant that is proportional to $\mu L/d^4$, where $\mu$ is the fluid viscosity, L is the length of the flow restrictor, d is the diameter of the restrictor. If the geometry (L and d) of the flow restriction is fixed and known, the time interval $\Delta t$ for a known pressure drop may be linearly proportional to the viscosity $\mu$ of the fluid and/or constants that depend on such viscosity. Thus, such viscosity or viscosity dependent constants may be determined by sensing the pressure at the selected locations between the upstream and downstream of the flow restriction before and after valve closure for a known time interval, assuming that temperature during such time interval is constant. Such viscosity may then be used to determine a more accurate measurement of the actual flow rate to the patient and for comparison to the desired flow rate as previously described above. In addition, monitoring the variation of pressure decay time during infusion could be useful for monitoring and detecting any abnormal condition. As an example, a sudden increase in decay time signals a flow blockage. On the other hand, a sudden reduction in decay time signals a shunting around the flow restrictor.

Prior to actual determination of an unknown viscosity, the system described above may be calibrated by first flowing a calibration fluid through the system. The decay time, $\Delta t_1$, of the calibration fluid such as water or air, which has a known viscosity, $\mu_1$, is automatically measured. Although calibration may be performed, the present invention is not intended to be limited to or required such calibration. If calibration is employed, then a fluid with an unknown viscosity, $\mu_2$, may be determined by the following equation:

$$\mu_2 = \mu_1 \ast \Delta t_2 / \Delta t_1$$

Where $\mu_1$ is the viscosity of the calibration fluid; $\mu_2$ is the viscosity of the delivery fluid; $\Delta t_1$ is the decay time of the calibration fluid; and $\Delta t_2$ is the decay time of the delivery fluid.

Figure 20:
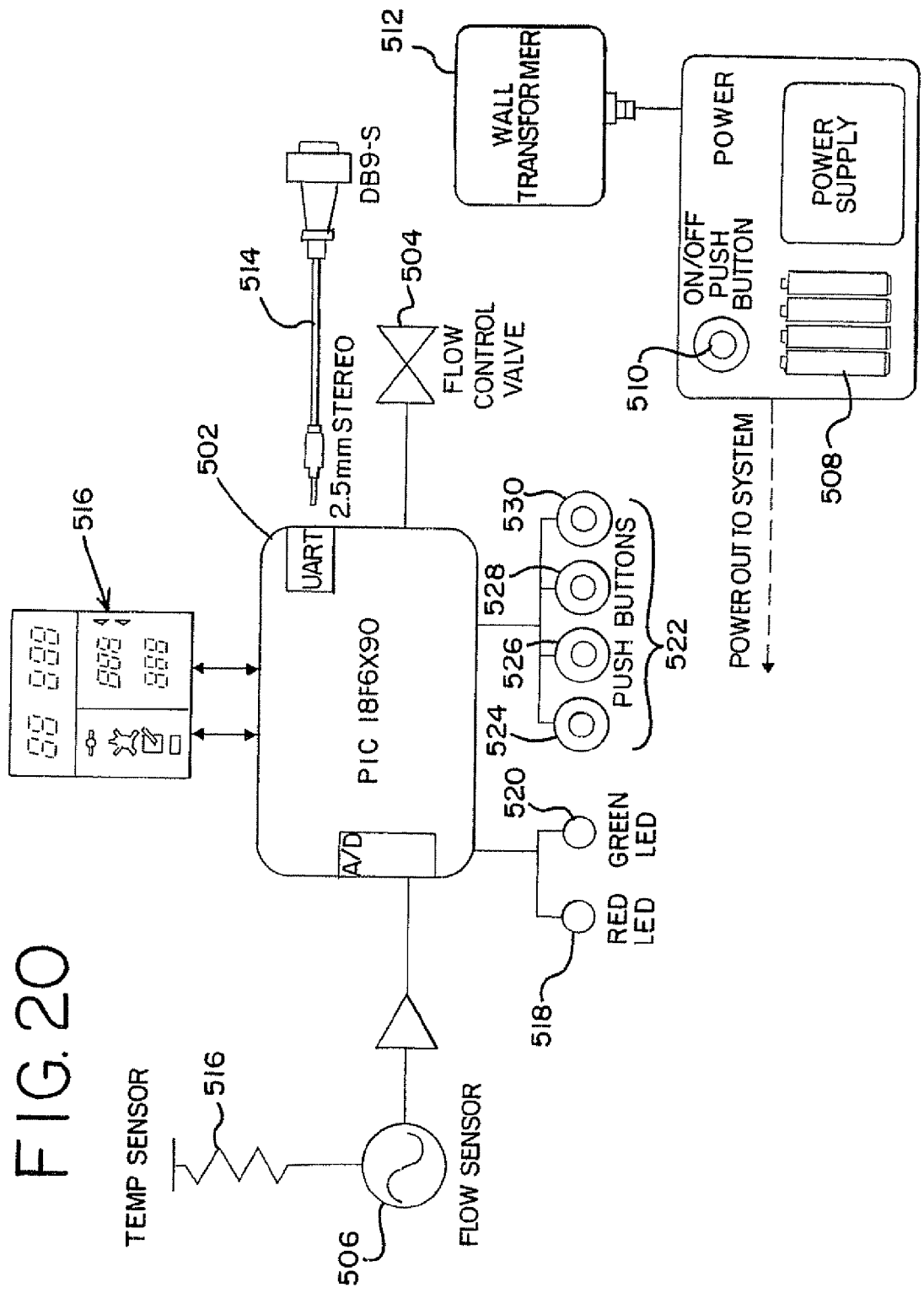
FIG. 20 is a schematic diagram showing an ambulatory fluid delivery system in accordance with a third embodiment of the present invention which includes a flow sensor, a flow valve, a temperature sensor, a user/patient interface, a power supply, and a connector for transferring fluid information to or from the system.

Optionally, the present invention may employ a temperature sensor or other temperature measuring device such as a thermocouple, thermistor and the like, as shown and described in FIG. 20 for measuring the temperature of the fluid. Such temperature sensor may be employed for determining the viscosity so as to avoid variations in viscosity due to a change in temperature. It is noted that the temperature of fluid may be controlled so that it is substantially constant to avoid variations in viscosity due to temperature. Alternatively, if the temperature of the fluid varies over the time interval during which viscosity is determined, then the system may automatically recalibrate so as to adjust the value of the viscosity based upon sensed differences in temperature. The temperature may be monitored and any variation in viscosity due to temperature may be calculated as a correction factor to the measured decay time. Other modifications are also possible.

Control System

As previously described, the illustrated control system 8 in FIG. 1 includes a display screen 26 in schematic form. Turning to a more specific example of a display screen in FIG. 2, the indicator or display screen 122 includes various fluid flow information or conditions. At the top center, the display screen 122 indicates the actual fluid flow rate or "FLOW RATE" (in ml/hr), at the left side in FIG. 2, and the total fluid volume or "AMT DEL", at the right side in FIG. 2. Below and to the left side, the display screen 122 includes graphical icons including: a flow sensor status icon, as represented next to the illustrated label, "SENSOR STATUS"; a flow status icon labeled next to "FLOW STATUS"; an edit mode icon labeled next to "EDIT MODE"; and a battery status icon labeled next to "BATTERY STATUS". The "SENSOR STATUS" icon may graphically indicate when a sensor malfunction is detected. The "FLOW STATUS" may indicate fluid flow status by an intermittently flashing fluid symbol if fluid is flowing to the patient or may indicate that fluid is not flowing such as by a cross-out fluid symbol. The "EDIT MODE" may indicate, if present, that the system is being programmed for a particular flow profile or, if not present, that the system is performing a fluid delivery infusion to a patient.

Below and to the right side of the display screen 122 in FIG. 2, other flow information may be displayed such as a bolus or maximum amount delivered during the flow profile or "BOLUS AMT", a bolus time at which the bolus amount was delivered or "BOLUS TIME" (in min), a patient control management (PCM) time that may record the time interval from a patient activated control of the flow profile or "PCM LOCKOUT" (in min), as will be described later. Variations of this information may be displayed and/or in combination with other information. It is contemplated that the flow information may be displayed in any orientation or design and may be numerical, graphical or other.

Turning to FIG. 20, components of a further embodiment of a controller 500 are shown in diagrammatic form which, among other features as described below, includes a display screen similar to that shown and described in FIG. 2. Similar to previously described embodiments, the controller 500 may include a printed circuit board 502, a flow valve 504, a flow sensor 506, and a power source such as batteries 508 or transformer 512 for an electrical wall outlet, with a power control switch 510.

The system may include an input/output port for connection to an external connector 514 to allow for transfer of data to/from the control system 500 and an external device such as a computer for downloading or uploading of flow information. Such information may include flow history information during a particular flow profile, including actual flow rate and pressure measurements from the control system and/or allow a history of several flow profiles to be downloaded for one or more patients.

The control system 500 may further include a temperature sensor 516 for measuring the temperature of the fluid. Such temperature sensor 516 is preferably in electrical communication with the control module 502 and may be used, as described above to determine fluid viscosity and improve the accuracy of measurement of the actual flow rate based on variations in temperature. The temperature sensor may be located within any of the control systems described herein or may be externally associated with such control system.

In FIG. 20, an indicator module or display screen 516 provides for a numerical or graphical display of flow information or conditions. The control system 500 may include flow status visual indicators 518 and 520 that may be respectively associated with off and on fluid flow conditions. By way of example in FIG. 20, the indicators 518, 520 may be color coded LED's, e.g., red and/or green, that are respectively associated with a "no flow" condition, where no fluid is flowing to the patient, and a "flow" condition, where fluid is flowing to the patient. A single flow status visual indicator 128 is also shown in FIG. 2, which may indicate flow status such as be changing color, or otherwise providing an indicating signal, as appropriate to "flow" or "no flow" conditions.

The control system 500 in FIG. 20 further includes a patient controllable interface, generally indicated at 522, which may include a plurality of actuators such as buttons 524, 526, 528, 530. As shown in the more detailed user/patient interface in FIG. 2, a plurality of actuators 132, 134, 136 and 138 such as push buttons or the like allow for user and/or patient adjustment of flow conditions, as will be described later. Although four actuators or push buttons are illustrated in FIGS. 2 and 20, any number of actuators may be used.

Figure 21:
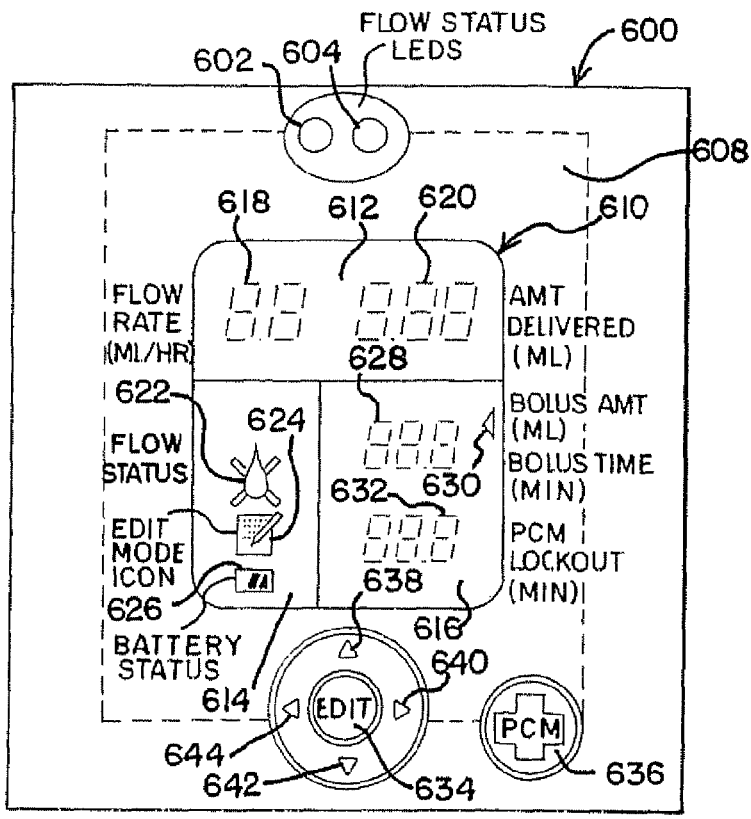
FIG. 21 is a front view of an indicator module for a control system, such as shown in FIG. 2, showing an edit mode during which fluid flow is stopped and flow conditions such as an initial fluid flow rate may be set by a user.

Turning to FIG. 21, an alternate indicator module, generally indicated at 600, may be employed in any of the control systems described herein. FIG. 21 shows and "edit mode" in which a user may program the control system for a particular fluid delivery therapy. The "edit mode" is preferably employed by the user such as a doctor or pharmacist for programming of the system to operate according to a preset flow profile. In such "edit mode," the user may program various flow conditions such as an initial flow rate, a basal or sustained flow rate and/or a flow rate that changes over time, a bolus or maximum flow rate, a desired flow rate as well as other flow conditions.

In FIG. 21, the indicator module 600 may include two flow status LEDs 602 and 604 which correspond to "flow" and "no flow" conditions such as described and shown in FIG. 20. All or a portion of the indicator module 600 may include a generally planar front surface 608, which provides a display screen 610 for displaying various fluid flow information conditions. In FIG. 21, the display screen 610 may be divided into a plurality of sections such as a top section 612, a bottom left section 614 and a bottom right section 616. The top section 612 may include flow information such as the actual flow rate 618, which may be determined as described herein, and further may include the total amount of fluid 620 delivered to the patient. The bottom left section 614 may include other fluid flow information such as a flow status icon 622, an edit mode icon 624, and a battery status icon 626.

During the "edit mode", the flow status icon 622 includes an "X" symbol that corresponds to one type of "no flow" condition through the system. Other types of "no flow" conditions will be described below. As also shown in FIG. 21, the edit mode icon 624 is displayed to indicate that the system may allow for the user to enter desired fluid flow therapy conditions such as a desired flow rate and/or other flow information conditions. The bottom right section 616 may include flow information such as a bolus fluid flow amount 628 or other fluid volume that may be delivered during a relatively short or instantaneous amount of time. Such bolus amount generally is delivered at a greater or maximum flow rate than the flow rate just prior to the bolus or alternatively is delivered at a maximum flow rate. The bottom right section 616 may also display information as to a bolus time interval that may be measured from when the bolus is activated or delivered. The display may toggle between indicating the bolus amount and bolus time interval, depending on an arrow 630 that indicates which information is between displayed. The bolus time may be preprogrammed by the control system and/or preset by the user that prevents patient activation of a bolus event until such preprogrammed or preset period has elapsed. The bottom right section 616 may also include a patient controlled management PCM lockout time 632, which may be measured from a patient activation, i.e., to increase or decrease flow and/or otherwise control fluid flow. The PCM time may automatically measured and compared to a preprogrammed or preset time interval to prevent another patient activation, e.g., to increase fluid flow, until a preset period has elapsed.

An edit control 634 and a PCM control 636 may allow adjustment to flow fluid rate and/or flow profile by the user and/or patient. Actuators and/or controls 638, 640, 642 and 644 may further allow for programming of or adjustment to the flow profile by the user and/or patient. One or more of such controls or actuators may allow for the system to be toggled between the "edit mode" during which fluid delivery is stopped and a "patient mode," as shown in FIG. 22, which allows for the fluid delivery to the patient and may allow adjustments in the fluid flow based on patient activation.

Figure 22:
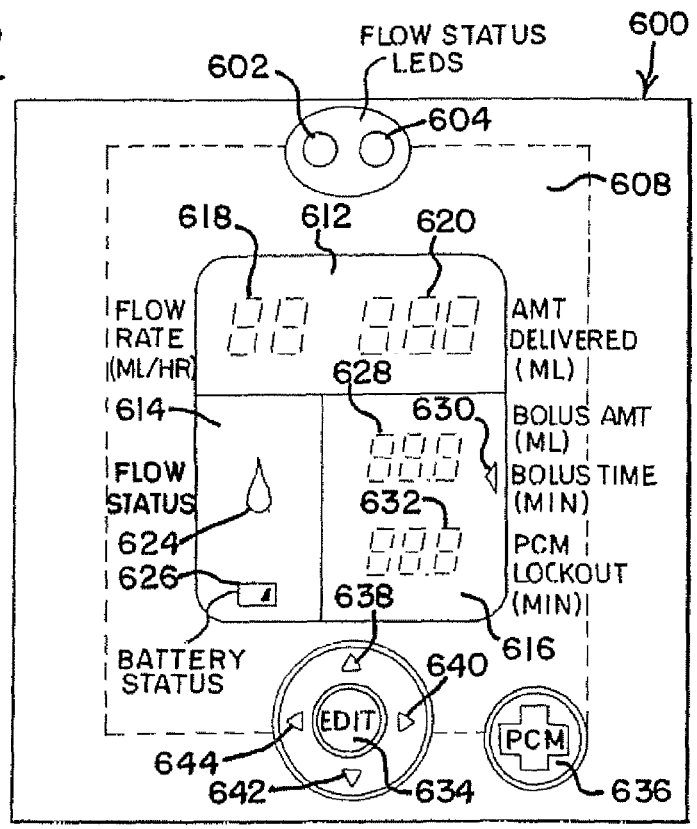
FIG. 22 is a front view of an indicator module of a control system, similar to FIG. 21, except showing a patient mode during which fluid flow may be provided to a patient and/or fluid flow may be controlled by the patient.

In FIG. 22, the control system is shown in a "patient mode" during which the patient may be permitted to control the flow or to allow control within preprogrammed or preset limits. The display screen 610 is similar to the display screen shown in FIG. 21 except that the flow status icon 622 indicates a "flow" condition in which fluid is flowing through the system although it is possible for the system to indicate a change in the flow status icon to indicate a "no flow" condition. Examples of some types of "no flow" conditions may include when the total desired amount of fluid volume has been infused to the patient, when the infusion fluid source is empty, when a malfunction in the valve operation has occurred, and/or when the flow path is occluded. As shown in FIG. 22, the edit mode icon 624 is not displayed. Also, in such "patient mode," the patient may initiate a bolus and/or basal amount using one or more actuators 638, 640, 642 and 644, in accordance with features as described further below.

Reusable Controller and Disposable Fluid Delivery Flow Set

Figures 23, 24:
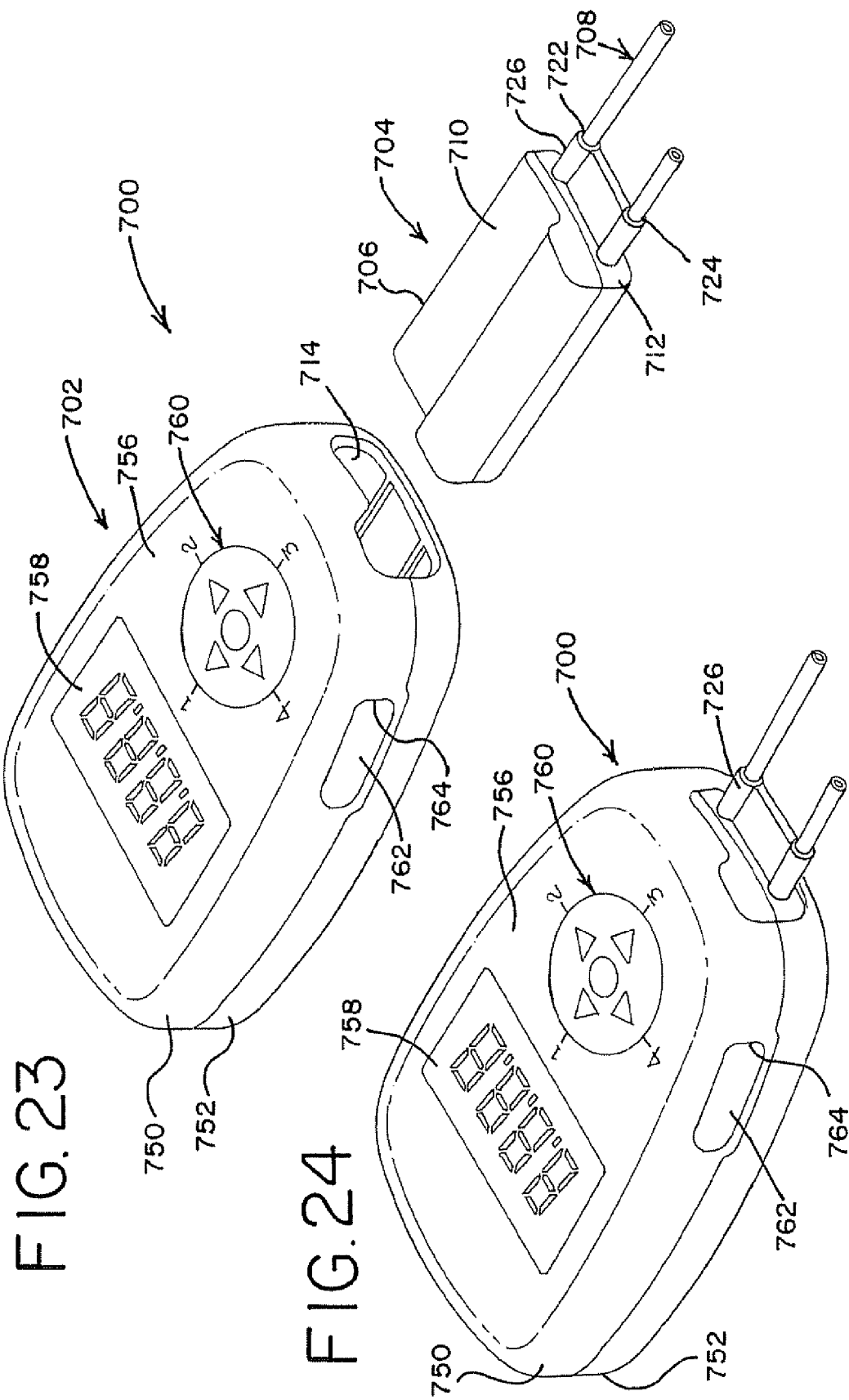
FIG. 23 is a perspective view of another ambulatory fluid delivery system in accordance with a fourth embodiment of the present invention, showing a reusable controller and a removable disposable flow set that is shown removed from the controller.
FIG. 24 is a perspective view of the system of FIG. 23 showing the reusable controller and the disposable flow set removably received therein.

Turning to FIGS. 23-30, a further embodiment of a fluid delivery system is illustrated which may be used for ambulatory patients. The system, generally indicated at 700, includes a durable, reusable controller 702 and a disposable fluid flow delivery set or circuit, generally indicated at 704. As shown in FIGS. 23-24, the reusable controller 702 is intended for repeated use and does not directly contact the fluid being administered to the patient while the disposable flow set 704, through which the fluid flows, is intended for one-time use only. By way of example and not limitation, such system 700 may be employed to delivery a pain medication, a peripheral nerve block agent, an analgesic or other anesthetic agent and/or another fluid such as by a flow profile that delivers a decreasing amount of fluid over a selected time interval. It is contemplated that other types of flow profiles may be employed depending on the specific needs of the patient.

Disposable Fluid Delivery Flow Set

The disposable fluid flow set 704 generally includes a flow control module 706 and a fluid flow path 708, preferably in the form of plastic tubing, similar to the fluid flow path in FIGS. 1-3, for communicating between a fluid source and a patient. The flow control module 706 is preferably attached to and part of the disposable flow set 704 and is adapted to be removably received by the reusable controller 702.

As shown in more detail in FIGS. 26-27, the flow control module 706 includes first and second housing portions 710 and 712 that generally enclose flow control components discussed in more detail below. As illustrated, the flow control module is attached to the tubing of the flow path 708, which is routed through the various flow control components. The module is connected to the reusable controller 702 by insertion into a module interface or receiving station 714 in the form of recess or cavity. The shape and configuration of the flow control module may vary depending on the design requirements. By way of example and not limitation, in FIGS. 23 and 25, shape and configuration of the flow control module 706 may be non-symmetrical, and the receiving station complementarily shaped, so that the module can only be inserted in a single orientation and/or avoid improper assembly of the flow system 700. With reference to FIG. 26, it may be seen that the flow control module 706 has a notch 716, which may be located on one or both sides of the module 706 defined in the surfaces of one or both of the first and second housing portions 710, 712. Each notch 716 may include an engagement surface 718 (see FIG. 30) and a sloped surface 720 (also in FIG. 30) and such surfaces of the notch are preferably shaped and configured to engage complementary projecting surfaces within the reusable controller to latch the module and controller together when the module is inserted in the receiving station 714.

The disposable set 704, and more specifically the flow control module 706 includes inlet and outlet 722 and 724 that are each associated with the tubing that forms the fluid flow path 708. More specifically, the tubing itself may be routed through module 706 or may be attached to separate inlet and outlet ports on the flow control module. A stress relief 726 may be associated with one or both of the inlet and outlet ports 722, 724 to reduce stress or occlusion of such ports, and/or provide a gripping surface for assisting the user or patient to insert or remove the flow control module 706.

As best seen in FIGS. 26-27, the disposable flow set 704 includes a flow control valve, generally indicated at 728 such as the type shown in FIGS. 9-11 or FIGS. 12-14 and described above, and a flow sensor module 730, such as shown in FIGS. 4-8 and as described above. As such, the flow control valve 728 preferably employs a shape memory activator for moving the valve between closed and open positions upon passage of electrical current therethrough. The flow sensor module 730 may include a flow (or differential pressure sensor) sensor 732 and a flow restrictor 734 through which the fluid flows. In the embodiment shown in FIGS. 26 and 27, it may seem that the tubing forming flow path 708 is routed through a channel or slot 735 in the flow control valve housing similar to that shown in FIGS. 9-11. The tubing is then connected to inlet 736 of the flow sensor 732, and a continuation of tubing is attached to outlet 738.

To provide any needed electrical power to the flow control module 706 and to provide a data or signal line to the reusable controller 702, conductive terminals 740 and 742 extend from the end of the module for mating with cooperative terminals within the receiving station 714 of the controller when the flow control module is inserted into the station (see FIG. 29).

Reusable Controller

In FIGS. 23-25, the illustrated controller 702 includes a first housing portion 750 and a second housing portion 752. The reusable controller 702 preferably defines the module interface or receiving station 714 that provides the receiving cavity for receiving the disposable flow control module 706 of the disposable flow set 704, in one side wall of the controller. As noted above, the station 714 and the module 706 preferably have a complementary non-symmetrical shape that allows insertion of the module into the cavity in only one position, such as shown in FIGS. 23 and 25.

The first housing portion 750 includes a front surface 756 which may include a flow information indicator or display screen 758 and/or a user/patient interface module, generally indicated at 760. The illustrated interface module 760 includes a plurality of flow controls, actuators or buttons, labeled as 1, 2, 3 and 4, that, when activated, may provide different flow profiles in response to the medication needs of the patient, as described further below. Actuators 762 may be located at each side of the controller 702, projecting through a complementary opening 764 formed in each side of the housing portions 750, 752. As described later, the actuators are movable by compressing or squeezing the together to mechanically release the flow control module for removal from the receiving station 714.

As best seen in FIGS. 28-29, the reusable controller 702 includes various internal components similar to those previous described above, such as a printed circuit board 766 and associated memory devices and microprocessor(s); display components 758; user input devices, an energy source 768 and/or other components. The energy source 768 may include one or more batteries (or, alternatively, an external power supply) that are electrically connected via an electrical contact for supplying power to the controller and/or the PCB. The internal controller components are shown arranged in a compact, stacked orientation at the top or upper portion of the reusable controller 702 in FIGS. 28-29 with the receiving station 714 being defined in a lower or bottom side edge portion for receiving the disposable flow control module 706, although other arrangements are also possible.

The reusable controller 702 may include an actuator arm 770 for removably connecting the flow set 704. The actuator arm 770 includes a first end 772 and a second end 774. The first end 772 may be pivotably mounted inside the controller 702 such as, for example, by attachment to a sleeve 776 for relative pivotable movement about the respective pivot 778. At a location intermediate the ends, the arm 770 attached to a separate sleeve 780, which receives a post member 782 and is pivotable about the post member. The actuator arm 770 curves outwardly between the two pivot locations and is accessible through each opening 764 of the housing portions 750, 752 in FIGS. 23-24. The actuator arm 770 is preferably made, at least in part, of a flexible resilient material so that application of compressive force to the actuators 762 allows for the actuator arm to move or flex inwardly from the housing portions 750, 752 and thereby cause pivotable movement of the second end 774 about the pivot 778. In the illustrated embodiment, two actuator arms 770 are used on opposite sides of the controller, and only one may also be sufficient to hold the flow control model 706 in this receiving station 714. The application of force to the actuators 762 may be applied simultaneously to both actuators 762 by the user's thumb or forefinger so as to move the actuators 762 simultaneously.

As shown in FIG. 30, the second or free end 774 of each actuator arm 770 extends through a respective opening 792 formed in opposing side walls defining the station 714. The second end 774 includes an inwardly extending hook-like projection 794 for extending through the opening 792. The projection 794 includes a taper lead surface 796, which allows the control module 706 to force the arm outwardly as it is inserted into the receiving station 714. In other words, during insertion of the flow control module, the free end 774 is pivoted by engagement with the module from a first position, as shown in solid lines in FIG. 30, to a second position, as shown in dashed lines in FIG. 30. Upon complete insertion of the control module 706, the free end 774 returns, via resilient biasing force of the arm 770 itself, to a position engaging the module to prevent inadvertent withdrawal. Each notch 716 of the flow set 704 preferably is located for alignment with the respective free end 774 so that the module 706 may be inserted into the reusable controller 702 with the gripping attachment 726 preferably being disposed outside of the controller 702 to assist in withdrawal of the spent module. Although such flow set is shown as being inserted into the controller near the bottom thereof in a generally upwards insertion direction, other locations and orientations are also possible.

System and Methods for Patient Controlled Fluid Delivery

Although not limited to pain management, further aspects of the present invention make it particularly well suited for controlling medical fluid flow for patient pain management. By way of example and not limitation, any of the above described controllers may be adapted to provide a selected flow rate or flow profile that varies or remains constant over a selected time period in accordance with a desired fluid therapy. The controller may be adapted for use for a plurality of different therapies and allow for selection of a particular therapy by the health professional or patient. For example, the physician and/or patient may select the actual flow rate or flow profile and the duration of the flow profile. Further, in accordance with previously described features, the actual flow rate may be controlled and/or the viscosity, temperature and other flow conditions may be determined so that the actual flow rate may be accurately controlled within acceptable tolerances to provide a desired flow rate for the selected therapy. Such a controller preferably may also allow for patient control or variation of the flow profile during use, if desired by the patient.

Figure 31:
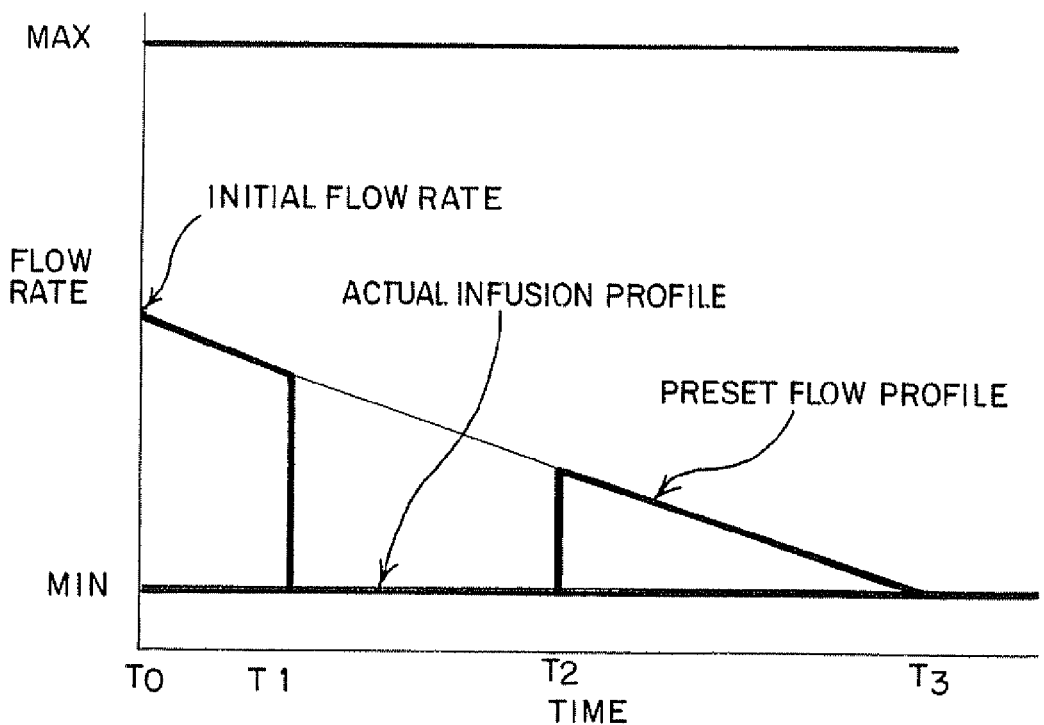
FIG. 31 is a flow profile graph showing flow rate (in ml/hr) versus time (in seconds) in accordance with one example of a fluid delivery therapy that may be provided by the present invention, which allows the patient to decrease fluid flow from a preset flow profile for a selected time interval and to return to the preset flow profile at the end of such time interval.

Turning to FIG. 31, the illustrated flow profile is one example of a pain management or "nerve-block" analgesia therapy in which the patient is administered an infusion fluid that is intended to block sensed levels of pain while still conscious. Numerous other flow profiles are possible and may depend on the type of fluid, the patient's health, the type of surgery employed on the patient and/or the recommended medical treatment. It is contemplated that the illustrated flow profile or others may be utilized with any of the embodiments described herein and preferably the embodiment in FIGS. 23-30.

In FIG. 31, a first flow mode or "preset flow profile" may include an initial flow rate and a sustained flow rate that decreases linearly with time from the initial flow rate to a final or minimum flow rate. The "preset flow profile" in FIG. 31 is one example of a basal-type infusion to the patient, although other flow profiles are also possible. By "basal" it is meant that the fluid flow to the patient includes a relatively lower flow rate or flow profile over an extended time period in contrast to a bolus-type infusion, which provides a relatively higher flow rate or flow profile over a relatively shorter or instantaneous time period, as described further in connection with the example shown in FIG. 32.

The illustrated basal or "preset flow profile" in FIG. 31 may be set by the healthcare professional or other user and/or programmed by the control system according to preset parameters or a combination thereof. The illustrated basal or "preset flow profile" may be beneficial for administering a local analgesic to a patient during a post-operative period, in which the initial flow rate corresponds generally to a relatively higher sensed level of pain by the patient and the flow profile gradually decreases or tapers from the initial flow rate as the patient's pain level generally decreases during the post-operative period. By way of example and not limitation, the initial flow rate may be varied between approximately 2 and 12 mL/hr, although such initial flow rate may also depend on the patient and the patient's initial pain level. For reference purposes in FIG. 31, the initial flow rate occurs at time $T_0$ and the preset flow rate decreases automatically from the initial flow rate to the final flow rate or minimum flow rate at time $T_3$ within a preset time interval, such as for example, a post-operative period of up to about 72 hours. Other variations in the flow profile, such as profiles having a non-linear or varying slope, and/or profiles having varying duration are also possible.

In FIG. 31, a second flow mode of the flow profile includes an "actual infusion profile" that provides an instantaneous decrease in the actual flow rate at a first time T1 preferably in response to patient activation of the patient controllable interface, as described above. More particularly, patient activation may be provided by the patient pressing one or more of the actuators 30 in FIG. 1, actuators 132, 134, 136, 138 in FIG. 2, actuators 524, 526, 528, 530 in FIG. 20 or actuators 1, 2, 3, 4 in FIG. 23, as shown and described above. It is also possible that such actuators may require that the patient actuate or press such actuator twice in succession within a relatively limited time frame as confirmation of that activation is desired and/or to avoid inadvertent actuation. Other modifications and alterations are also possible. Such actuators may be differentiated from one another by color-code or other symbols or indicia that provide an indication to the user, which is representative to the patient's a sensed level of pain.

In FIG. 31, such patient activation creates a relatively constant and lower fluid flow rate for a time interval ΔT1 between time T1 and time T2. Such patient-activated or actual flow profile may deviate from the prior basal or "preset flow profile" relatively instantaneously, as shown in FIG. 31, or may be more gradual. The illustrated "actual infusion profile" may be provided, for example, to a patient that has an adverse reaction to the fluid and that needs a reduction in the flow rate for a certain time period until the reaction has subsided. Alternatively, such actual flow profile may provide a minimum or keep-open flow rate to a patient that is experiencing little to no pain for a selected time period. Other "actual infusion profiles" that limit flow are also possible, including but not limited to a flow profile that, upon patient activation, stops the fluid flow to the patient for a preset period of time. Any number of variations are possible with a programmable controller dependent on the needs of the patient and prescribed treatment by the health professional.

The time interval ΔT1 between about T1 and T2 may be a predetermined period of time such as for example between about 2 hours and 4 hours although other time periods are possible. At the end of such predetermined time interval, the flow profile at about second time T2 may return or resume the prior or preset flow profile. Return to the preset flow profile may be instantaneous as shown in FIG. 31 or may occur more gradually over a selected time period. Fluid flow may then continue according to the preset flow profile until a final time T3 unless the patient activates another variation in the flow profile. The preset flow profile at the final time T3 may terminate when the fluid source is exhausted such as by detecting a pressure drop in the fluid flow path that results from an empty fluid source, for example, a pressure drop that is less than about 0.5 psi that is not the result of an occluded flow path. Alternatively, the controller may be programmed to automatically shut off upon reaching a targeted time period or desired administered fluid volume such as when a preset flow profile period has elapsed and/or a desired fluid volume has been delivered to the patient.

During the time interval ΔT1, the system may be programmed to prevent patient attempts to make changes to the flow profile for a certain period of time. This may be referred to as a "lockout time period" because the patient is, in effect, locked out of the system with respect to further fluid flow changes after patient activation. For example in FIG. 31, a lockout period may begin at time T1 such that attempted patient activation of other actuators or controls would not result in any change to the flow profile in FIG. 31 until such lockout period has elapsed. The time interval ΔT1 may be preset, such as for example, between about 2 to 4 hours during which other patient changes may not be allowed, although other lockout time periods are also possible.

Figure 32:
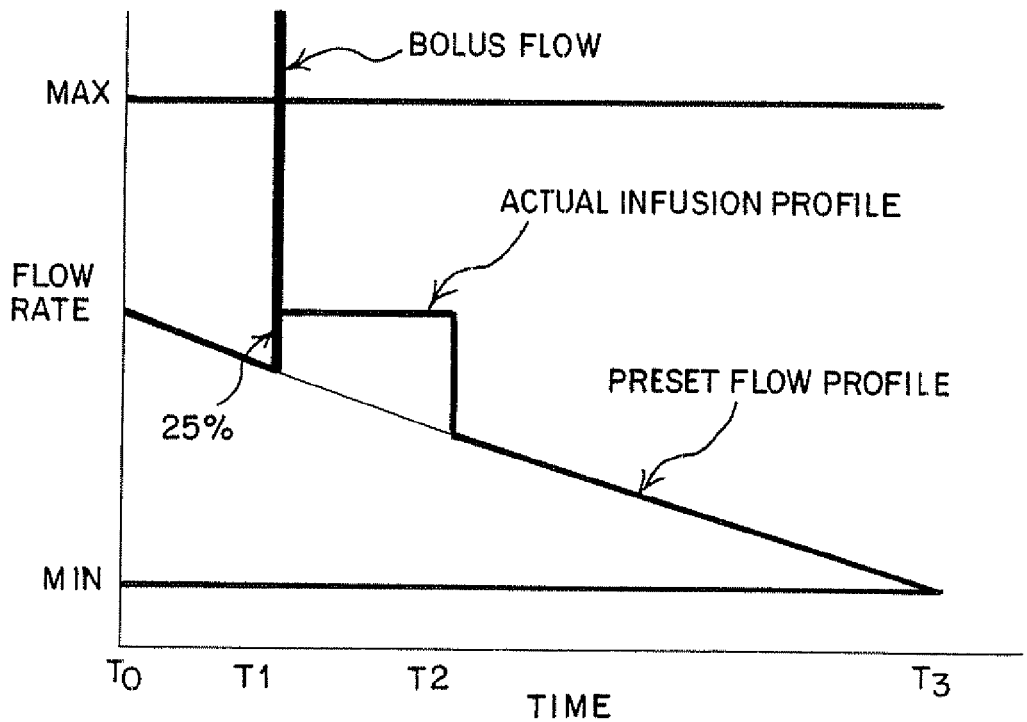
FIG. 32 is a flow profile graph showing flow rate (in ml/hr) versus time (in seconds) in accordance with another example of a fluid delivery therapy that may be provided by the present invention, which allows the patient to increase fluid flow from a preset flow profile to provide an initial bolus fluid flow and a sustained or basal fluid flow rate during a selected time interval and to return to the preset flow profile at the end of such time interval.

In FIG. 32, an alternate flow profile is illustrated, which also includes a "preset flow profile" similar to FIG. 31 in accordance with a basal-type infusion. During a first flow mode defined between a time T0 to a first time T1, fluid flows at an initial flow rate at time T0 and subsequently flows at a sustained basal flow rate that linearly decreases from time T0 to time T1. At time T1, patient activation initiates a second flow mode, such as by activating or pressing a different actuator of the patient controllable interface than that used for FIG. 31, such as one of actuators 30 in FIG. 1, actuators 132, 134, 136, 138 in FIG. 2, actuators 524, 526, 528, 530 in FIG. 20 or actuators 1, 2, 3, 4 in FIG. 23, as shown and described above. Such second or patient-activated flow mode generally deviates from the "preset flow profile" resulting in one or more changes to the actual flow rate of fluid received by the patient.

At time T1, the second or patient activated flow mode of the flow profile includes an "actual infusion profile" that provides an increase in the actual flow rate at a first time T1 preferably in response to patient activation of the patient controllable interface, as described above. The illustrated increase in FIG. 32 initially provides a "bolus flow" or a relative maximum fluid volume that is delivered to the patient at time T1 by a relatively rapid and/or instantaneously flow. One example of a bolus flow may include a fluid volume of about 2 to 5 mL that may be delivered to the patient during a time period that varies between about 0 and 5 minutes, although other variations are also possible. The bolus flow may be delivered at a relatively high or maximum flow rate as indicated in FIG. 32. The amount and duration of the bolus flow may vary.

In FIG. 32, after time T1 or after the "bolus flow", the second or patient-activated flow mode then provides an "actual infusion profile" at an increased fluid level, which is preferably responsive to an increased pain level sensed by the patient. In FIG. 32, the "actual infusion profile" includes a patient-activated sustained or basal-type fluid flow rate that remains constant after time T1 until a time T2, although other flow rates are also possible. Such sustained flow rate is relatively greater than the basal flow rate of the "preset flow profile" just prior to patient activation at time T1. As shown in FIG. 32, the patient-activated sustained flow rate may be sustained over a relatively longer portion of the time interval ΔT1 than the duration of the bolus flow. Such sustained flow rate may be sustained until time T2, which provides for return to the "preset flow profile" until a final time T3, unless the patient activates another variation in the flow profile.

Other flow profiles may be provided for different sensed pain levels that are experienced by the patient. Preferably, each actuator 30 (in FIG. 1), 132, 134, 136, 138 (in FIG. 2), 524, 526, 528, 530 (in FIG. 20) or 1, 2, 3, 4 (in FIG. 23) provides an indicator, numeric, graphical or otherwise, of a pain level so that the patient may select an actuator that is proportional to the sensed level of pain. By way of example and not limitation, patient selection of button 1 in FIG. 23 may provide the reduced actual flow in FIG. 31. Patient activation of a different button such as one of actuators 2, 3 or 4 in FIG. 23 may provide the increased actual infusion profile in FIG. 32, which upon such activation, the control module proportionally increases the flow rate to approximately 25% greater than the preset flow profile flow rate at the time of such patient activation. A plurality of different actuators may be employed, as shown and described in the embodiments, and appropriately labeled to correspond to different or graduated pain levels so that each actuator, when activated, provides a changed flow profile that is suitable to the—sensed pain level of the patient. Other flow profiles are possible based on different sensed pain levels of the patient. By way of example and not limitation, the patient may select from actuators, such as actuators 1, 2, 3 or 4 in FIG. 23, that may provide different decreased flow rates and/or that may provide a bolus flow and subsequent basal flow rates that proportionally increase the fluid flow rate to relatively higher sensed pain levels of about 25% or 50%, respectively, for the time interval between time T1 and time T2. One of the actuators 1, 2, 3 or 4 may correspond to a patient activation that stops fluid flow until active restart of the control system. Other variations are also possible.

Similar to FIG. 31, there may be a patient "lockout time period" that prevents patient activation during a selected period of time after patient activation of the "actual infusion profile" with associated bolus and basal flow rates shown in FIG. 32. For example, during the first time interval ΔT1 and after the initial maximum or bolus flow volume, the system may be programmed with a preset "bolus lockout time period". If, for example, the bolus lockout time period is set at about 1 hour and the first time interval ΔT1 is about 2 hours, then the bolus lockout time in FIG. 32, may elapse at time T1.5 to allow a subsequent bolus flow if activated thereafter. During first time interval ΔT1, there also may be a "basal lockout time period" to prevent changes to the patient-activated sustained or basal flow rate until such lockout time period has elapsed. In FIG. 32, if, for example, the "basal lockout time period" for the patient-activated sustained flow rate is about 2 hours and the first time interval ΔT1 is about 2 hours, then the patient may not change such sustained or basal flow rate until the lockout time period has elapsed at time T2. Variations to these lockout time periods are possible. In the example shown in FIG. 32, the "actual infusion profile" automatically returns to the "preset flow profile" at about time T2 although another patient activations may be initiated as described above. It is contemplated that there may be numerous combinations and permutations of flow profiles that may be employed, apart from those described and shown in FIGS. 31-32, with even greater combinations of the bolus and basal flows and lockout times and these may vary depending on several factors, as discussed above.

In one example, the preset flow profile may include an initial or basal flow rate that is set between about 3 and 5 ml/hr and a final flow rate of about 2 ml/hr, with a maximum or bolus flow rate of about 10 ml/hr. Another example of a flow profile includes an initial or basal flow rate that is set between about 6 and 7 ml/hr, a final flow rate of about 3 ml/hr and a maximum or bolus flow rate of about 12 ml/hr. A further example of a flow profile includes an initial or basal flow rate between about 8 and 12 ml/hr, a final flow rate of abut 3 ml/hr and a maximum or bolus flow rate of about 12 ml/hr. Other flow profiles are also possible.

The preset flow profile may be set such as by allowing the healthcare professional and/or patient to program one or more of the flow conditions. By way of example, the user and/or patient may set one or more of the initial or basal flow rate, the final flow rate, the rate of change of the flow rate, the maximum or bolus flow rate, the bolus amount, the total delivered flow volume, the basal lockout time, the bolus lockout time and/or other flow parameters or conditions. Alternatively, the controller may be programmed with a plurality of preset parameters and/or allow profiles and allow the user to select a desired flow profile from among such profiles. For example, the controller may be programmed to allow the user to select only an initial or basal flow rate and/or a rate of change of such flow rate such as an initial flow rate between about 3 and 12 ml/hr, which increments or decreases 1 ml/hr. The remaining parameters may be automatically selected and/or preprogrammed based on the user selected initial flow rate. Other variations are also possible including allowing the flow profile to be set by a healthcare professional and not subject to change by the patient.

As can be seen from the above description, the present invention has several different aspects, which are not limited to the specific structures shown in the attached drawings and which do not necessarily need to be used together. For example, it is preferred but not required to employ the viscosity determination in association with the flow rate detection. Variations of these concepts or structures may be embodied in other structures for carrying out delivery of medical fluids or other fluids without departing from the present invention as set forth in the appended claims.

The invention claimed is

1. A medical fluid delivery system for determining viscosity of a fluid, the system comprising:
    a fluid flow path for communicating between a source and a patient:
    a fixed flow restriction in the fluid flow path;
    a flow valve operatively associated with the fluid flow path upstream of the fixed flow restriction, such valve being movable between a first position, which allows fluid flow through the path, and a second position, which limits fluid flow through the fluid flow path; and
    a control module operatively associated with the fluid flow path for sensing a fluid pressure difference within the fluid flow path at a selected location upstream of the flow restriction when the valve moves from the first position to the second position and for determining viscosity of the fluid based at least in part on such fluid pressure difference; and
    wherein the fluid pressure difference is measured during movement of the valve from the first position to the second position, and the second position includes stopping fluid flow through the fluid flow path upstream of such selected location.

2. The system of claim 1, wherein the control module is operatively associated with the fluid flow path for determining an actual fluid flow rate in the fluid flow path based, at least in part, on the determined viscosity of the fluid.

3. The system of claim 1, further comprising a flow sensor for sensing the fluid pressure difference.

4. The system of claim 3, wherein the fluid pressure difference is measured between a first sensing at a first time at the selected location and a second sensing at a later second time at the selected location and the control module determines viscosity based, at least in part, on any pressure difference at such selected location that occurs in the time interval between such first and second sensing independent of flow rate.

5. The system of claim 1, wherein the flow path has a selected size upstream of the flow restriction and the flow restriction defines a flow path size smaller than the selected size such that the flow restriction defines a reduced flow path area.

6. The system of claim 4, wherein the time interval is a decay time, and the control module monitors the decay time to detect an abnormal condition.

* * * * *